United States Patent [19]

Kawazu et al.

[11] 4,053,609
[45] Oct. 11, 1977

[54] PENICILLINS AND PROCESSES FOR PREPARING THE SAME

[75] Inventors: Mitsutaka Kawazu; Mitsuyoshi Wagatsuma, both of Urawa; Masahiko Seto, Asaka; Toshikazu Miyagishima, Wako; Totaro Yamaguchi, Yono; Satoshi Ohshima, Iwatsuki, all of Japan

[73] Assignee: Tanabe Seiyaku Co., Ltd., Osaka, Japan

[21] Appl. No.: 711,858

[22] Filed: Aug. 5, 1976

[30] Foreign Application Priority Data

Sept. 12, 1975 United Kingdom ............... 37525/75
Dec. 27, 1975 Japan .................. 50-157873
Dec. 27, 1975 Japan .................. 50-157874
Dec. 29, 1975 Japan .................. 50-157920

[51] Int. Cl.² .................... C07D 499/68; A61K 31/43
[52] U.S. Cl. ............................... 424/271; 260/239.1
[58] Field of Search ....................... 260/239.1; 424/271

[56] References Cited

U.S. PATENT DOCUMENTS 3,325,477 6/1967 Fosher et al. ....................... 260/239.1
3,340,252 9/1967 Alburn et al. ....................... 260/239.1
3,923,788 12/1975 Fenes et al. ....................... 260/239.1

Primary Examiner—Gerald A. Schwartz
Attorney, Agent, or Firm—Bierman & Bierman

[57] ABSTRACT

A compound of the formula:

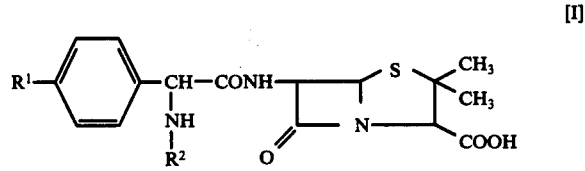

wherein $R^1$ is hydrogen or hydroxy, $R^2$ is a group of the formula: $-CO-CH(NH_2)-CH_2COR^3$ or $-COCH_2-CH(NH_2)-COR^3$, and $R^3$ is selected from the group consisting of hydroxy, lower alkylamino, di-lower alkylamino, lower alkoxy and hydroxy-lower alkylamino, or $R^3$ is amino when $R^1$ is hydroxy. Several methods of preparing the compound [I] are also disclosed. The compound [I] and a pharmaceutically acceptable salt thereof are useful as antimicrobial agents.

43 Claims, No Drawings

PENICILLINS AND PROCESSES FOR PREPARING THE SAME

This invention relates to new penicillins and processes for preparing the same. More particularly, it relates to a 6-(D-2-acylamido-2-phenylacetamido)penicillanic acid of the formula:

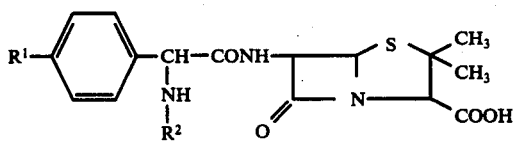

[I]

wherein $R^1$ is hydrogen or hydroxy, $R^2$ is a group of the formula: $-CO-CH(NH_2)-CH_2COR^3$ or $-COCH_2-CH(NH_2)-COR^3$, and $R^3$ is selected from the group consisting of hydroxy, lower alkylamino, di-lower alkylamino, lower alkoxy and hydroxy-lower alkylamino, or $R^3$ is amino when $R^1$ is hydroxy. Pharmaceutically acceptable salts of the compound [I] are also included within the scope of the present invention.

U.S. Pat. Nos. 3,268,513 and 3,340,252 disclose that 6-[D-2-(DL-2-aminoglutaramido)-2-phenylacetamido]-penicillanic acid is prepared by reacting 6-(D-2-amino-2-amino-2-phenylacetamido)penicillanic acid with DL-glutamine, and said glutaramido derivative shows antimicrobial activity against both gram-positive and gram-negative bacteria. On the other hand, German Patent Application No. 1934783 discloses that 6-[D-2-(L-2-amino-3-carbamoylpropionamido)-2-phenylacetamido]-penicillanic acid is prepared by condensing 6-aminobenzylpenicillin with biphenylisopropyloxycarbonyl-L-asparagine, followed by removing the protecting group therefrom.

Accordingly the present invention provides novel penicillins which are useful as antibacterial agents, nutritional supplements in animal food, and as chemotherapeutic agents in poultry and mammals, including man, in the treatment of infectious diseases caused by gram-positive and gram-negative bacteria. Namely, the penicillanic acid compound [I] of the present invention shows potent antimicrobial activity against a wide variety of microorganisms and at the same time can be effectively absorbed upon either oral or parenteral administration to man and animals. In particular, the penicillanic acid compound [I] shows potent antimicrobial activity against bacteria belonging to the genera Pseudomonas and Staphylococcus. For example, 6-[D-2-(D-2-amino-3-N-methylcarbamoyl-propionamido)-2-p-hydroxy-phenylacetamido]penicillanic acid exhibits minimum inhibitory concentrations (M.I.C.) (Agar dilution method, Heart-infusion agar) of about 12.5 μg/ml against Pseudomonas aeruginosa $A_3$. On the other hand, the M.I.C. of Sulbenicillin [i.e., disodium 6-(D-2-sulfonyl-2-phenylacetamido)penicillanate], 6-[D-2-(DL-2-aminoglutaramido)-2-phenylacetamido]penicillanic acid and 6-[D-2-(L-2-amino-3-carbamoyl-propionamido)-2-phenylacetamido]penicillanic acid against said microorganism are 12.5, 50 and more than 100 μg/ml, respectively. The antimicrobial activity of 6-[D-2-(D-2-amino-3-N-methylcarbamoyl-propionamido)-2-p-hydroxyphenylacetamido)-2-p-hydroxy-phenylacetamido]penicillanic acid invention against Staphylococcus aureus ATCC 6538P and St. epidermidis 10131R is also about 2 to 4 times stronger than those of Sulbenicillin and 6-[D-2-(L-2-amino-3-carbamoyl-propionamido)-2-phenylacetamido]penicillanic acid. The penicillanic acid compound [I] of the present invention may further exhibit potent antimicrobial activity against other gram-positive and gram-negative bacteria such as those belonging to the general Streptococcus, Escherichia, Klebsiella, Salmonella and Bacillus. Furthermore, the toxicity of the compound [I] of the invention is remarkably low. For example, when 6-[D-2-(D-2-amino-3-N-methylcarbamoyl-propionamido)-2-p-hydroxyphenylacetamido]-penicillanic acid is administered intravenously to mice at the dose of 10,000 mg/kg, not a single mouse died for a period of 14 days after the administration.

The penicillanic acid compound [I] of the present invention can be used for pharmaceutical use either as the free acid or as a salt thereof. Pharmaceutically acceptable non-toxic salts of the compound include, sodium, potassium, calcium, aluminium, ammonium and substituted ammonium salts, e.g., salts of such non-toxic amines as trialkylamines including triethylamine, procaine, dibenzylamine, N-benzyl-β-phenethylamine, 1-ephenamine, N,N'-dibenzylethylenediamine, dehydroabiethylamine, N,N'-bis-dehydroabiethylethylenediamine, and other amines which have been used to form salts with benzylpenicillin. The penicillanic acid compound is extremely soluble in water and can be administered either orally or parenterally (e.g., intravenously, intramuscularly, subcutaneously). The daily dose for an adult patient is about 0.25 to about 20 g, especially about 0.5 to 10 g, with the preferred dose being 4 g. Further, the compound [I] may be used in the form of a pharmaceutical preparation containing the same compound in conjunction or admixture with a pharmaceutical excipient suitable for enteral or parenteral administration. Suitable excipients include gelatin, lactose, glucose, sodium chloride, starch, magnesium stearate, talcum, and vegetable oil. The pharmaceutical preparations may be in solid form such as tablets, coated tablets, pills or capsules; or in liquid form such as solutions, suspensions or emulsions. They may be sterilized and/or may also contain additives such as stabilizing, wetting or emulsifying agents.

The penicillanic acid compound [I] of the present invention can be prepared by the steps of:

i. condensing a 6-(D-2-amino-2-phenylacetamido)-penicillanic acid compound of the formula:

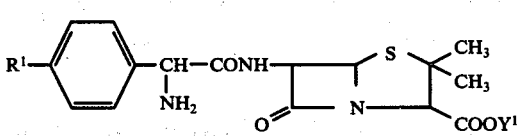

[II]

wherein $Y^1$ is hydrogen or a protecting group and $R^1$ is the same as defined above, with a N-protected-amino acid of the formula:

$R^{2'} - OH$   [III]

wherein $R^{2'}$ is a group of the formula: $-CO-CH(NHZ)-CH_2COR^3$ or $-COCH_2-CH(NHZ)-COR^3$, Z is a protecting group and $R^3$ is the same as defined above, or a reactive derivative thereof to give a 6-(D-2-acylamido-2-phenylacetamido)penicillanic acid compound of the formula:

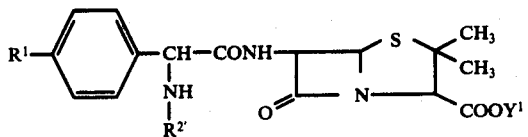

wherein $R^1$, $R^{2'}$ and $Y^1$ are the same as defined above, or
ii. condensing a D-2-acylamido-phenylacetic acid of the formula:

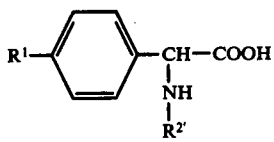

wherein $R^1$ and $R^{2'}$ are the same as defined above, or a reactive derivative thereof with a 6-aminopenicillanic acid compound of the formula:

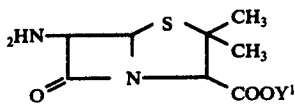

wherein $Y^1$ is the same as defined above, to give the 6-(D-2-acylamido-2-phenylacetamido)penicillanic acid compound [IV], and then (iii) removing the protecting group(s) from the compound [IV]. On the other hand, the compound [I] of the invention in which $R^3$ is hydroxy may also be prepared by the steps of condensing the compound [II] with a N-protected-amino acid of the formula:

$R^{2''}$-OH     [VII]

wherein $R^{2''}$ is a group of the formula: —CO—CH(NH-Z)—CH$_2$COOY$^2$ or —COCH$_2$-CH(NHZ)—COOY$^2$, $Y^2$ is a protecting group and Z is the same as defined above, or a reactive derivative thereof to give a 6-(D-2-acylamido-2-phenylacetamido)penicillanic acid compound of the formula:

[VIII]

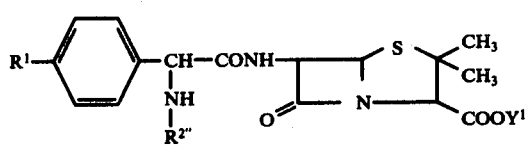

wherein $R^1$, $R^{2''}$ and $Y^1$ are the same as defined above, and then removing the protecting groups therefrom. Alternatively, the compound [I] of the present invention may be prepared by the steps of reacting an O-protected-natural penicillin of the formula:

[IX]

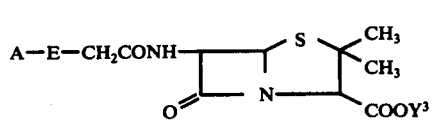

wherein A is alkyl, alkenyl, phenyl or substituted phenyl, E is single bond, sulfur atom or oxygen atom and $Y^3$ is a protecting group, with a phosphorus halide compound to give an iminohalide compound of the formula:

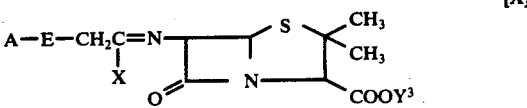

wherein X is halogen and A, E and $Y^3$ are the same as defined above, reacting the iminohalide compound [X] with a lower alkanol to give an iminoether compound of the formula:

[XI]

wherein $R^4$ is lower alkyl and A, E and $Y^3$ are the same as defined above, and if required, treating the iminoether compound [XI] with water to give the corresponding imidate compound, reacting the compound [XI] or its corresponding imidate compound with a lower alkoxycarbonyl ester of the D-2-acylamidophenylacetic acid [V] to give a 6-(D-2-acylamido-2-phenylacetamido)penicillanic acid compound of the formula:

[XII]

wherein $R^1$, $R^{2'}$ and $Y^3$ are the same as defined above, and then removing the protecting groups from the compound [XII].

Examples of the protecting group represented by the symbol $Y^1$ or $Y^3$ include benzyl, succinimidomethyl, phthalimidomethyl, phenacyl, trimethylsilyl and 2,2,2-trichloroethyl groups. On the other hand, benzyl is suitable as the protecting group $Y^2$. Suitable examples of the protecting group Z include o-nitrophenylsulfenyl, benzyloxycarbonyl and 1-methyl-2-lower alkoxycarbonylvinyl. The penicillanic acid compounds [II] and [VI] in which $Y^1$ is hydrogen may be used for the reactions of the present invention in the form of either a free acid or a salt of said compound. Suitable examples of said salts include alkali metal salts such as sodium and potassium salts, and lower trialkylamine salts such as trimethylamine and triethylamine salts. Further, the starting compound [IX] includes, for example, phenacyl, benzyl, trimethylsilyl, trichloroethyl, phthalimidomethyl and succinimidomethyl esters of various natural penicillins. Penicillin G (benzylpenicillin), Penicillin K(n-heptylpenicillin), Penicillin X (p-hydroxybenzylpenicillin), Penicillin F (2-hentenylpenicillin), dihydro-Penicillin F (n-amylpenicillin), Penicillin AT (allylmercaptomethylpenicillin), Penicillin BT (butylthiomethyl-penicillin), Penicillin S (γ-chlorocrotylmercaptomethylpenicillin) and Penicillin V (phenoxymethylpenicillin) may be employed as the preferred natural penicillins. Suitable examples of group A may include alkyl of 4 to 6 carbon atoms (e.g., butyl, hexyl), alkenyl or haloalkenyl of 2 to 4 carbon atoms (e.g., vinyl, 1-propenyl,2-chloro-1-propenyl, 1-butenyl), phenyl and monohydroxyphenyl.

The condensation reaction of the penicillanic acid compound [II] with the amino acids [III] or [VII] as well as the condensation reaction of the phenylacetic acid [V] with the penicillanic acid compound [VI] can be readily accomplished. For example, said condensation reactions are preferably carried out in the presence of diphenylphosphoric azide [i.e., $N_3PO(OC_6H_5)_2$] in a solvent. A suitable temperature range is $-20°$ to $20°$ C, especially $-10°$ to $5°$ C. Preferably, there is the organic tertiary amine, such as trimethylamine or triethylamine present. Dimethylformamide, dimethylsulfoxide, chloroform and dichloromethane are suitable as the reaction solvent.

Alternatively, the acids [III], [V] and [VII] may be converted to the reactive derivative thereof prior to the condensation reactions mentioned above. Examples of the reactive derivative of these acids include the corresponding mixed anhydride (e.g., lower alkoxycarbonyl esters such as ethoxycarbonyl, isobutoxycarbonyl, tert.-butoxycarbonyl and tert.-amyloxycarbonyl; lower alkanoyl esters such as pivaloyl ester), active esters (e.g., esters with p-nitrophenol and N-hydroxysuccinimide) and azide. The mixed anhydrides of the acids [III], [V] and [VII] may be prepared in the conventional manner; for example, by reacting these acids with a lower alkoxycarbonyl halide (e.g., bromide, chloride) or a lower alkanoyl halide (e.g., bromide, chloride) at $-5°$ to $-40°$ C in the presence of an acid acceptor in a solvent. Chloroform, dichloromethane, dimethylsulfoxide, tetrahydrofuran and dimethylformamide are suitable for use as the solvent, and examples of the acid acceptor include N,N-dimethylaniline, N-methylmorpholine, Pyridine and so forth.

On the other hand, the active esters of the acids [III], [V] and [VII] may be prepared by reacting these acids with p-hydroxyphenol or N-hydroxysuccinimide at $-10°$ to $30°$ C in the presence of a dehydrating agent (e.g., dicyclohexylcarbodiimide) in a solvent (e.g., tetrahydrofuran, dioxane, diglyme). Further, the azide may be prepared by reacting the hydrazide of these acids with sodium nitrite in a dilute mineral acid (e.g., sulfuric acid). The condensation reactions of the penicillanic acid compound [II] with the thus-obtained reactive derivatives of the amino acids [III] or [VII] are carried out at a temperature of $40°$ to $-30°$ C, especially at $5°$ to $-15°$ C, in a solvent. Dimethylformamide, chloroform, tetrahydrofuran and methylene chloride are suitable as the reaction solvent. The condensation reaction of the penicillanic acid compound [VI] with the reactive derivative of the phenylacetic acid [V] can also be carried out under the same conditions as above.

The reaction of the O-protected-natural penicillin [IX] with the phosphorus halide compound is readily conducted in a solvent. Suitable examples of the phosphorus halide compound include phosphorus pentachloride, phosphorus pentabromide, phosphorus oxychloride and phosphorus tribromide. The reaction may be carried out at $-10°$ to $-40°$ C in the presence of an organic tertiary amine. 1,2-Dichloroethane and chloroform are suitable for use as the reaction solvent. Dimethylaniline, N-methylmorpholine, pyridine and so forth may be used as the organic tertiary amine. After the above-mentioned reaction is completed, a lower alkanol is added to the reaction solution thus obtained (i.e., a solution containing the iminohalide compound [IX]), and the mixture is further stirred at $-10°$ to $-45°$ C, whereby the iminoether compound [XI] is obtained. Methanol, ethanol, propanol and butanol may be suitably employed as the lower alkanol. The iminoether compound [XI] thus obtained can be directly used for the subsequent coupling reaction with th lower alkoxycarbonyl ester of the D-2-acylamido-phenylacetic acid [V]. If required, however, the iminoether compound [XI] may be treated, prior to said coupling reaction, with water at $0°$ to $-5°$ C to give the corresponding imidate compound. The subsequent coupling reaction of the iminoether compound [XI] or its corresponding imidate compound with the lower alkoxycarbonyl ester of the D-2-acylamido-phenylacetic acid [V] is preferably carried out at a temperature of $0°$ to $-30°$ C, especially at $-5°$ to $-15°$ C, in a solvent. 1,2-Dichloroethane and chloroform are suitable as the reaction solvent.

Removal of the protecting group or groups from the 6-(D-2-acylamido-2-phenylacetamido)penicillanic acid compounds [IV], [VIII] and [XII] can be effected by any appropriate procedures depending upon the kinds of the protecting group or groups employed. For example, when o-nitrophenylsulfenyl is used as the protecting group Z, said group can be removed by reacting the compound [IV], [VIII] or [XII] with about 2 to 3 molar equivalents of a thioamide in a solvent. Suitable examples of the thioamide include thioacetamide, thiobenzamide, thiourea and 2-mercapto-5-methyl-1,3,5-thiadiazole. It is preferred to carry out the reacton at a temperature of $40°$ to $0°$ C, especially at $20°$ to $10°$ C. Ethyl ether, tetrahydrofuran, dioxane, a lower alkanol (e.g., methanol, ethanol) or a mixture of these solvents are suitable as the reaction solvent. When the protecting group Z is benzyloxycarbonyl and/or each one of the protecting groups $Y^1$, $Y^2$ and $Y^3$ is benzyl, the removal of said protecting group or groups may be conducted by shaking the compound [IV], [VIII] or [XII] in hydrogen gas in the presence of a catalyst. This catalytic hydrogenation is preferably carried out at a temperature of $40°$ to $0°$ C, especially at $20°$ to $10°$ C, under atmospheric pressure. Preferred examples of the catalyst include palladium-$BaCO_3$, palladium-charcoal and palladium-black. Lower alkanols such as methanol and ethanol are suitable as the reaction solvent. On the other hand, when the protecting group Z is 1-methyl-2-lower alkoxycarbonylvinyl and/or each one of the protecting groups $Y^1$ and $Y^3$ is trimethylsilyl, said group or groups may be removed by treating with a dilute mineral acid (e.g., 0.5 to 1 % hydrochloric acid) at a temperature of $5°$ to $10°$ C in a solvent (e.g., methyl ethyl ketone, methyl isobutyl ketone, dioxane). Further, when phenacyl, phthalimidomethyl or succinimidomethyl is employed as the protecting group $Y^1$ or $Y^3$, said group may be removed by reacting it with an alkali metal salt of a thiol compound of thiophenol. This reaction is preferably carried out at $10°$ to $-10°$ C in a solvent (e.g., tetrahydrofuran, isopropanol). 2-Ethylhexyl ester of 2-mercaptoacetic acid is suitably employed as the thiol compound. When the protecting group $Y^1$ or $Y^3$ is 2,2,2-trichloroethyl, this group is removed by reducing the compound [IV], [VIII] or [XII] with a mixture of 90% formic acid zinc powder in conventional manner. The reaction may be carried out at a temperature of $10°$ to $-5°$ C.

The starting compounds [III], [V] and [VII] of the present invention can be easily obtained by conventional methods. For example, the N-protected-amino acid [III] is prepared by reacting an amino acid of the formula: R³—COCH₂-CH(NH₂)—COOH or R³—CO-CH(NH₂)—CH₂COOH, wherein R³ is the same as defined above, with a compound of the formula: Z-X, wherein Z and X are the same as defined above. The reaction may be preferably carried out at 0° to 40° C in the presence of an acid acceptor (e.g., sodium carbonate, potassium carbonate, sodium hydroxide) in a solvent such as water, tetrahydrofuran, dioxane or a mixture thereof. The starting compound [VII] may also be prepared by reacting an amino acid of the formula: Y²OCO-CH₂CH(NH₂)-COOH or YOCO-CH(NH₂)-CH₂COOH, wherein Y² is the same as defined above, with a compound of the formula Z—X, wherein Z and X are the same as defined above, in the same manner as above. Further, the D-2-acylamido-phenylacetic acid [V] may be prepared by condensing a phenylacetic acid compound of the formula:

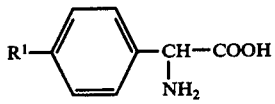

wherein R¹ is the same as defined above, with a reactive derivative (e.g., N-hydroxysuccinimide ester) of the N-protected amino acid of the formula: R²'-OH, wherein R²' is the same as defined above. This condensation reaction is carried out at 40° to −30° C in a solvent (e.g., dimethylformamide, tetrahydrofuran, methylene chloride).

Practical and preferred embodiments of the present invention are shown in the following examples. In this specification and claims, the terms "lower alkyl" and "lower alkoxy" should be interpreted as referring to straight or branched alkyl and alkoxy groups having one to six carbon atoms.

EXAMPLE 1

1. A solution of 1.5 g (11.8 millimoles) of DL-2-amino-3-N-methylcarbamoyl-propionic acid hydrochloride (i.e., DL-N'-methyl-asparagine HCl) in 16 ml of water is neutralized with potassium carbonate, and 5 ml of tetrahydrofuran are added thereto. 2.5 g of o-nitrophenylsulfenyl chloride are added to the solution at 5° to 10° C. Then, the mixture is stirred at the same temperature for 2 hours. During the reaction, the mixture is kept at a slightly alkaline pH (pH 8) with potassium carbonate. 10 ml of water are added to the reaction mixture, and insoluble materials are filtered off. The filtrate is washed twice with ethyl acetate, acidified with citric acid and then extracted three times with 50 ml of ethyl acetate. The ethyl acetate extracts are washed with water, dried and evaporated to remove solvent. 2.8 g of DL-2-(o-nitrophenylsulfenylamino)-3-N-methylcarbamoyl-propionic acid are obtained. M.p. 151° - 152° C.

2. 1.5 g (5 millimoles) of DL-2-(o-nitrophenylsulfenylamino)-3-N-methylcarbamoyl-propionic acid are dissolved in 30 ml of tetrahydrofuran. 1.14 g (5.5 millimoles) of dicyclohexyl-carbodiimide and 632 mg (5.5 millimoles) of N-hydroxysuccinimide are added to the solution at 0° to 5° C, and the mixture is stirred at the same temperature for 16 hours. Insoluble materials are filtered off. Then, the filtrate is evaporated at 20° C under reduced pressure to remove the solvent, and the crystalline precipitates thus obtained are washed with a mixture of benzene ether. 1.2 g of N-[DL-2-(o-nitrophenylsulfenylamino)-3-N-methylcarbamoyl-propionyloxy]-succinimide are obtained as crystals. M.p. 133° - 135° C.

3. 450 mg (1.13 millimoles) of N-[DL-2-(o-nitrophenylsulfenylamino)-3-N-methylcarbamoyl-propionyloxy]succinimide and 6.05 mg (1.3 millimoles) of 6-[D-2-amino-2-(p-hydroxyphenyl)-acetamido]penicillanic acid triethylamine salt are dissolved in a mixture of 10 ml of chloroform and 15 ml of dimethylformamide. The solution is stirred at 0° to 5° C for 16 hours. The solution is then evaporated at about 30° C under reduced pressure to remove the solvent. Ether is added to the residue, and the precipitate thus obtained is collected by filtration. 700 mg of 6-[D-2-(DL-2-(o-nitrophenylsulfenylamino)-3-N-methylcarbamoyl-propionamido)-2-p-hydroxyphenylacetamido]penicillanic acid are obtained as yellow caramel.

Infrared absorption spectrum:
$\nu_{max}^{nujol}$: 3270, 1775, 1720, 1645 cm⁻¹

4. 710 mg (1,1 millimoles) of 6-[D-2-(DL-2-(o-nitrophenylsulfenylamino)-3-N-methylcarbamoyl-propionamido)-2-p-hydroxyphenylacetamido]penicillanic acid and 450 mg (3.3 millimoles) of thiobenzamide are dissolved in a mixture of 20 ml of ethanol and 5 ml of tetrahydrofuran. The solution is then stirred at room temperature for 30 minutes. The reaction solution is evaporated at about 30° C under reduced pressure to remove solvent. The residue thus obtained is mixed with 20 ml of tetrahydrofuran, and precipitates are collected by filtration. The precipitates thus obtained are dissolved in 10 ml of aqueous tetrahydrofuran. 30 ml of ethyl acetate are added thereto, and then the aqueous layer is separated therefrom. After washing twice with a mixture of tetrahydrofuran and ethyl acetate, the aqueous layer is freeze-dried. 450 mg of 6-[D-2-(DL-2-amino-3-N-methylcarbamoyl-propionamido)-2-p-hydroxyphenylacetamido]penicillanic acid are obtained as colorless powder. M.p. 15° - 198° C (decomp.)

Infrared absorption spectrum:
$\nu_{max}^{nujol}$: 3280, 1760, 1650, 1595 cm⁻¹

Thin layer chromatography:
Rf = 0.43 (Silica gel plate, Solvent: n-butanol-acetic acid-water (4 : 1 : 1))

Infrared absorption spectrum of the potassium salt:
$\nu_{max}^{nujol}$: 3300, 1760, 1650, 1595 cm⁻¹

EXAMPLE 2

1. 3 g (23.6 millimoles) of D-2-amino-3-N-methylcarbamoyl-propionic acid hydrochloride (i.e., D-N'-methyl-asparagine HCl), 5 g of o-nitrophenylsulfenyl chloride, 30 g of water, 10 ml of tetrahydrofuran and 12 g of potassium carbonate are treated in the same manner as described in Example 1-(1). 5 g of D-2-(o-nitrophenylsulfenylamino)-3-N-methylcarbamoyl-propionic acid are obtained. M.p. 134° - 136° C.

2. 1.57 g (5.2 millimoles) of D-2-(o-nitrophenylsulfenylamino)-3-N-methylcarbamoyl-propionic acid, 1.3 g of dicyclohexylcarbodiimide, 788 mg of N-hydroxysuccinimide and 15 ml of tetrahydrofuran are treated in the same manner as described in Example 1-(2). 1.8 g of N-[D-2-(o-nitrophenylsulfenylamino)-3-N-methylcarbamoyl-propionyloxy]succinimide are obtained. M.p. 126° - 128° C.

3. 800 mg (2 millimoles) of N-[D-2-(o-nitrophenyl-sulfenylamino)-3-N-methylcarbamoyl-propionyloxy]succinimide and 932 mg (2 millimoles) of 6-[D-2-amino-2-(p-hydroxyphenyl)acetamido]penicillanic acid triethylamine salt are dissolved in 15 ml of dimethylformamide. The solution is stirred at 0° to 5° C for 16 hours. After the reaction, the solution is treated in the same manner as described in Example 1-(3). 1.15 g of 6-[D-2-(D-2-(o-nitrophenylsulfenylamino)-3-N-methylcarbamoyl-propionamido)-2-p-hydroxyphenylacetamido]penicillanic acid are obtained as yellow powder. M.p. 165° - 167° C (decomp.)

4. 1.10 g (1.7 millimoles) of 6-[D-2-(D-2-(o-nitrophenylsulfenylamino)-3-N-methylcarbamoyl-propionamido)-2-p-hydroxyphenylacetamido]penicillanic acid and 830 mg (6.0 millimiles) of thiobenzamide are dissolved in a mixture of 15 ml of methanol and 5 ml of tetrahydrofuran. The solution is stirred at room temperature for 45 minutes. Then, the reaction solution is treated in the same manner as described in Example 1-(4). 700 mg of 6-[D-2-(D-2-amino-3-N-methylcarbamoyl-propionamido)-2-p-hydroxyphenylacetamido]penicillanic acid are obtained as a colorless powder. M.p. 198° - 201° C (decomp.)

Infrared absorption spectrum:
$\nu_{max}^{nujol}$: 3280, 1760, 1660 cm$^{-1}$
Thin layer chromatography:
Rf = 0.43 (Silica gel plate, Solvent: n-butanol-acetic acid-water (4 : 1 : 1))
Infrared absorption spectrum of the potassium salt:
$\nu_{max}^{nujol}$: 3300, 1760, 1660, 1600 cm$^{-1}$

EXAMPLE 3

1. 4.5 g (36 millimoles) of L-2-amino-3-N-methyl-carbamoyl-propionic acid hydrochloride (i.e., L-N'-methyl-asparagine HCl), 7.6 g of o-nitrophenylsulfenyl chloride, 40 g of water, 20 ml of tetrahydrofuran and 18 g of potassium carbonate are treated in the same manner as described in Example 1-(1). 7 g of L-2-(o-nitrophenylsulfenylamino)-3-N-methylcarbamoyl-propionic acid are obtained. M.p. 132° - 135° C.

2. 3.2 g (11 millimoles) of L-2-(o-nitrophenylsulfenylamino)-3-N-methylcarbamoyl-propionic acid, 2.6 g of dicyclohexyl-carbodiimide, 1.6 g of N-hydroxysuccinimide and 35 ml of tetrahydrofuran are treated in the same manner as described in Example 1-(2). 3.5 g of N-[L-2-(o-nitrophenylsulfenylamino)-3-N-methylcarbamoyl-propionyloxy]succinimide are obtained. M.p. 127° - 129° C.

3. 792 mg (2 millimoles) of N-[L-2-(o-nitrophenyl-sulfenylamino)-3-N-methylcarbamoyl-propionyloxy]succinimide and 932 mg (2 millimoles) of 6-[D-2-amino-2-(p-hydroxyphenylacetamido]penicillanic acid triethylamine salt are dissolved in 15 ml of dimethylformamide. The solution is stirred at 0° to 5° C for 16 hours. After the reaction is completed, the solution is treated in the same manner as described in Example 1-(3). 1.05 g of 6-[D-2-(L-2-(o-nitrophenylsulfenylamino)-3-N-methylcarbamoyl-propionamido)-2-p-hydroxyphenylacetamido]penicillanic acid are obtained as caramel.

Infrared absorption spectrum:
$\nu_{max}^{nujol}$: 3260, 1775, 1720, 1635 cm$^{-1}$ 4. 1.00 g (1.55 millimoles) of 6-[D-2-(L-2-(o-nitrophenylsulfenylamino)-3-N-methylcarbamoyl-propionamido)-2-p-hydroxyphenylacetamido]penicillanic acid and 740 mg (5.4 millimoles) of thiobenzamide are dissolved in a mixture of 40 ml of methanol and 10 ml of tetrahydrofuran. The solution is stirred at room temperature fro 40 minutes. Then, the reaction solution is treated in the same manner as described in Example 1-(4). 620 mg of 6-[D-2-(L-2-amino-3-N-methylcarbamoyl-propionamido)-2-p-hydroxyphenylacetamido]-penicillanic acid are obtained. M.p. 197° - 200° C (decomp.)

Infrared absorption spectrum:
$\nu_{max}^{nujol}$: 3250, 1760, 1650 cm$^{-1}$
Thin layer chromatography:
Rf = 0.43 (Silica gel plate, Solvent: n-butanol-acetic acid-water (4 : 1 : 1))

EXAMPLE 4

1. 2.10 g (10 millimoles) of D-2-amino-3-N-isopropylcarbamoyl-propionic acid (i.e., D-N'-isopropyl-asparagine), 2.2 g of o-nitrophenylsulfenyl chloride, 20 ml of water, 20 ml of tetrahydrofuran and 2.0 g of potassium carbonate are treated in the same manner as described in Example 1-(1). 2.3 g of D-2-(o-nitrophenylsulfenylamino)-3-N-isopropylcarbamoyl-propionic acid are obtained. M.p. 146° - 147° C (decomp.)

2. 981 mg (3 millimoles) of D-2-(o-nitrophenylsulfenylamino)-3-N-isopropylcarbamoyl-propionic acid, 639 mg of dicyclohexylcarbodiimide, 356 mg of N-hydroxysuccinimide and 20 ml of tetrahydrofuran are treated in the same manner as described in Example 1-(2). 1.13 g of N-[D-2-(o-nitrophenylsulfenylamino)-3-N-isopropylcarbamoyl-propionyloxy]succinimide are obtained as crystals. M.p. 144° - 145° C (decomp.)

3. 699 mg (1.5 millimoles) of 6-[D-2-amino-2-(p-hydroxyphenyl)-acetamido]penicillanic acid triethylamine salt are dissolved in 10 ml of dimethylformamide at 3° to 5° C. 636 mg (1.5 millimoles) of N-[D-2-(o-nitrophenylsulfenylamino)-3-N-isopropylcarbamoyl-propionyloxy]succinimide are added to the solution, and the mixture is stirred at the same temperature for 2 hours. After the reaction, the mixture is poured into 50 ml of ice-water. Then the aqueous mixture is washed twice with 30 ml of ethyl acetate, acidified with citric acid and extracted three times with 30 ml of ethyl acetate. The combined extracts are washed three times with 20 ml of water, dried and evaporated at below 25° C under pressure to remove solvent. 950 mg of 6-[D-2-(D-2-(o-nitrophenylsulfenylamino)-3-N-isopropylcarbamoyl-propionamido)-2-p-hydroxyphenylacetamido]penicillanic acid are obtained as crystals. M.p. 152°-154° C (decomp.)

Infrared absorption spectrum:
$\nu_{max}^{nujol}$: 3275, 1780, 1730, 1640, 1620 cm$^{-1}$ 4. 920 mg (1.36 millimoles) of 6-[D-2-(D-2-(o-nitrophenylsulfenylamino)-3-N-isopropylcarbamoyl-propionamido)-2-p-hydroxyphenylacetamido]penicillanic acid are dissolved in a mixture of 20 ml of ethanol and 5 ml of tetrahydrofuran. 616 mg (4.5 millimoles) of thiobenzamide are added to the solution at room temperature, and the solution is stirred at the same temperature for one hour. The reaction solution is evaporated at below 25° C under reduced pressure to remove solvent. Ether is added to the residue, and crystalline precipitates are collected by filtration. After washed with tetrahydrofuran, the precipitates are dissolved in 50 ml of water. Then, the aqueous solution is washed twice with a solution of tetrahydrofuran and ethyl acetate (3 : 1), and further washed with ether and then freeze-dried. Ether is added to the freeze-dried powder, and the crystalline precipitates are collected by filtration. 620 mg of 6-[D-2-(D-2-amino-3-N-isopropylcarbamoyl-propionamido)-2-p-hydroxyphenylacetamido]penicillanic acid are obtained as crystals. M.p. 198°-200° C (decomp.)

Infrared absorption spectrum:
$v_{max}.^{nujol}$: 3250, 1760, 1650 cm$^{-1}$
Thin layer chromatography:
RF = 0.38 (Silica gel plate, Solvent: n-butanol-acetic acid-water (4 : 1 : 1))

EXAMPLE 5

1. 2.5 g (11 millimoles) of D-2-amino-3-N-n-butylcarbamoyl-propionic acid hydrochloride (i.e., D-N'-n-butyl-asparagine HCl), 2.2 g of o-nitrophenylsulfenyl chloride, 25 ml of water, 25 ml of tetrahydrofuran and 1.2 g of sodium hydroxide are treated in the same manner as described in Example 1-(1). 2.6 g of D-2-(o-nitrophenylsulfenylamino)-3-N-n-butylcarbamoyl-propionic acid are obtained. M.p. 143° - 144° C (decomp.)

2. 1.023 g (3 millimoles) of D-2-(o-nitrophenylsulfenylamino)-3-N-n-butylcarbamoyl-propionic acid, 639 mg (3.1 millimoles) of dicyclohexylcarbodiimide, 356 mg (3.1 millimoles) of N-hydroxysuccinimide and 20 ml of tetrahydrofuran are treated in the same manner as described in Example 1-(2). 1.04 g of N-[D-2-(o-nitrophenylsulfenylamino)-3-N-n-butylcarbamoyl-propionyl-oxy]succinimide are obtained. M.p. 135° - 136° C (decomp.)

3. 699 mg (1.5 millimoles) of 6-[D-2-amino-2-(p-hydroxyphenyl)-acetamido]penicillanic acid triethylamine salt, 657 mg (1.5 millimoles of N-[D-2-(o-nitrophenylsulfenylamino)-3-N-n-butylcarbamoyl-propionyloxy]succinimide and 10 ml of dimethylformamide are treated in the same manner as described in Example 4-(3). 1010 mg of 6-[D-2-(D-2-(o-nitrophenylsulfenylamino)-3-N-n-butylcarbamoyl-propionamido)-2-p-hydroxyphenylacetamido]-penicillanic acid are obtained as caramel.
Infrared absorption spectrum:
$v_{max}.^{nujol}$: 3275, 1770, 1725, 1640 cm$^{-1}$ 4. 980 mg (1.42 millimoles) of 6-[D-2-(o-nitrophenylsulfenylamino)-3-N-n-butylcarbamoyl-propionamido)-2-p-hydroxyphenylacetamido]penicillanic acid, 616 mg (4.5 millimoles) of thiobenzamide and 15 ml of ethanol are treated in the same manner as described in Example 4-(4). 570 mg of 6-[D-2-(D-2-amino-3-N-n-butylcarbamoyl-propionamido)-2-p-hydroxyphenylacetamido]-penicillanic acid are obtained as crystals. M.p. 188° - 191° C (decomp.)
Infrared absorption spectrum:
$v_{max}.^{nujol}$: 3270, 1760, 1650 cm$^{-1}$
Thin layer chromatography:
RF = 0.45 (Silica gel plate, Solvent: n-butanol-acetic acid-water (4 : 1 : 1))

EXAMPLE 6

1. 2.7 g (11 millimoles) of D-2-amino-3-N-n-hexyl-carbamoyl-propionic acid hydrochloride (i.e., D-N'-hexyl-asparagine HCl), 2.2 g of o-nitrophenylsulfenyl chloride, 30 ml of water, 25 ml of tetrahydrofuran and 1.2 g of sodium hydroxide are treated in the same manner as described in Examples 1-(1). 2.8 g of D-2-(o-nitrophenylsulfenylamino)-3-N-n-hexylcarbamoyl-propionic acid are obtained. M.p. 115° - 116° C (decomp.)

2. 1.11 g (3 millimoles) of D-2-(o-nitrophenylsulfenylamino)-3-N-n-hexylcarbamoyl-propionic acid, 639 mg (3.1 millimoles) of dicyclohexylcarbodiimide, 356 mg of N-hydroxysuccinimide and 20 ml of tetrahydrofuran are treated in the same manner as described in Example 1-(2). 1.23 g of N-[D-2-(o-nitrophenylsulfenylamino)-3-N-n-hexylcarbamoyl-propionyloxy]succinimide are obtained. M.p. 128° - 129° C (decomp.)

3. 699 mg (1.5 millimoles) of 6-[D-2-amino-2-(p-hydroxyphenyl)acetamido]penicillanic acid triethylamine salt, 699 mg (1.5 millimoles of N-[D-2-(o-nitrophenylsulfenylamino)-3-N-n-hexylcarbamoyl-propionyloxy]succinimide and 10 ml of dimethylformamide are treated in the same manner as described in Example 4-(3). 980 mg of 6-[D-2-(D-2-(o-nitrophenylsulfenylamino)-3-N-n-hexylcarbamoyl-propionamido)-2-p-hydroxyphenylacetamido]-penicillanic acid are obtained as caramel.
Infrared absorption spectrum:
$v_{max}.^{nujol}$: 3275, 1770, 1725, 1635 cm$^{-1}$ 4. 714 mg (one millimole) of 6-[D-2-(D-2-(o-nitrophenylsulfenylamino)-3-N-n-hexylcarbamoyl-propionamido)-2-p-hydroxyphenylacetamido]penicillanic acid, 472 mg (3.5 millimoles) of thiobenzamide and 10 ml of ethanol are treated in the same manner as described in Example 4-(4). 390 mg of 6-[D-2-(D-2-amino-3-N-n-hexylcarbamoyl-propionamido)-2-p-hydroxyphenylacetamido]-penicillanic acid are obtained as crystals. M.p. 186° - 189° C (decomp.)
Infrared absorption spectrum:
$v_{max}.^{nujol}$: 3250, 1770, 1655 cm$^{-1}$
Thin layer chromatography:
RF = 0.53 (Silica gel plate, Solvent: n-butanol-acetic acid-water (4 : 1 : 1))

EXAMPLE 7

1. 5 g (33 millimoles) of D-2-amino-3-carbamoyl-propionic acid (i.e., D-asparagine), 8.5 g of o-nitrophenylsulfenyl chloride, 40 ml of water, 20 ml of tetrahydrofuran and 5.5 g of potassium carbonate are treated in the same manner as described in Examples 1-(1). 6.7 g of D-2-(o-nitrophenylsulfenylamino)-3-carbamoyl-propionic acid are obtained. M.p. 163° C (decomp.)

2. 2.85 g (10 millimoles) of D-2-(o-nitrophenylsulfenylamino)-3-carbamoyl-propionic acid, 2.28 g of dicyclohexylcarbodiimide, 1.27 g of N-hydroxysuccinimide and 50 ml of tetrahydrofuran are treated in the same manner as described in Example 1-(2). 3 g of N-[D-2-(o-nitrophenylsulfenylamino)-3-carbamoyl-propionyloxy]-succinimide are obtained. M.p. 135 - 136° C (decomp.)

3. 380 mg (1.00 millimole) of N-[D-2-(o-nitrophenylsulfenylamino)-3-carbamoyl-propionyloxy]succinimide and 500 mg (1.07 millimoles of 6-[D-2-amino-2-(p-hydroxyphenylacetamido]-penicillanic acid triethylamine salt are dissolved in a mixture of 4 ml of chloroform and 4 ml of dimethylformamide. The solution is stirred at 0° to 5° C for 26 hours. After the reaction is completed, the solution is evaporated at about 30° C under reduced pressure to remove solvent. 10 ml of an aqueous 5% citric acid solution are added to the residue, and the mixture is extracted with a mixture of 20 ml of ethyl acetate and 10 ml of tetrahydrofuran. The extract is washed with water, dried and then evaporated at about 30° C under reduced pressure to remove solvent. 800 mg of 6-[D-2-(D-2-(o-nitrophenylsulfenylamino)-3-carbamoyl-propionamido)-2-p-hydroxyphenylacetamido]penicillanic acid are obtained as a crude product. This crude product is dissolved in a mixture of 2 ml of tetrahydrofuran and 8 ml of ethanol. 410 mg (3 millimoles) of thiobenzamide are added to the solution, and the solution is stirred at room temperature for 15 minutes. Then, the reaction solution is evaporated at about 30° C under reduced pressure. The residue thus obtained is mixed with 20 ml of tetrahydrofuran, and pale yellow precipitates are collected by filtration. The pecipitates are dissolved in 30 ml of water, insoluble materials are removed by filtration, and then the filtrate is freeze-dried. The colorless amorphous powder obtained is suspended in 3 ml of methanol. 100 mg (1.0 millimole) of triethylamine and 180 mg (1.0 millimole) of potassium 2-ethylhexanoate are added to the suspension. Then, 20 ml of ether are added thereto, and colorless precipitates are collected by filtration. 370 mg of potassium 6-[D-2-amino-3-carbamoyl-propionamido)-2-p-hydroxphenylacetamido]penicillanate are obtained. M.p. 213° - 215° C (decomp.)

Infrared absorption spectrum:
$\nu_{max.}^{nujol}$: 3300, 1760, 1660, 1590 cm$^{-1}$ Thin layer chromatography:
Rf = 0.30 (Silica gel plate, Solvent: n-butanol-acetic acid-water (4 : 1 : 1))

EXAMPLE 8

1. 594 mg (1.5 millimoles) of N-[DL-2-(o-nitrophenylsulfenylamino)-3-N-methylcarbamoyl-propionyloxy]-succinimide and 900 mg (2.0 millimoles) of D-α-aminobenzylpenicillin triethylamine salt are dissolved in a mixture of 25 ml of chloroform and 10 ml of dimethylformamide. The solution is stirred at 0° to 5° C for 17 hours. After the reaction, the solution is treated in the same manner as described in Example 1-(3). 870 mg of 6-[D-2-(DL-2-(o-nitrophenylsulfenylamino)-3-N-methylcarbamoyl-propionamido)-2-phenylacetamido]penicillanic acid are obtained as yellow crystals. M.p. 135° - 140° C(decomp.)

Infrared absorption spectrum:
$\nu_{max.}^{nujol}$: 3280, 1780, 1730, 1635 cm$^{-1}$ 2. 860 mg (1.35 millimoles) of 6-[D-2-(DL-2-o-nitrophenylsulfenylamino)-3-N-methylcarbamoyl-propionamido)-2-phenyl-acetamido]penicillanic acid and 547 mg (4.05 millimoles) of thiobenzamide are dissolved in a mixture of 50 ml of methanol and 10 ml of tetrahydrofuran. The solution is stirred at room temperature for 15 minutes. The reaction solution is then treated in the same manner as described in Example 1-(4). 580 mg of 6-[D-2-(DL-2-amino-3-N-methylcarbamoyl-propionamido)-2-phenylacetamido]penicillanic acid are obtained as colorless powder M.p. 193° - 195° C(decomp.)

Infrared absorption spectrum:
$\nu_{max.}^{nujol}$: 3250, 1760, 1645, 1590 cm$^{-1}$ Thin layer chromatography:
Rf = 0.45 (Silica gel plate, Solvent: n-butanol-acetic acid-water (4 : 1 : 1))

EXAMPLE 9

(1) 1.19 g (3 millimoles) of N-[D-2-(o-nitrophenylsulfenylamino)-3-N-methylcarbamoyl-propionyloxy]succinimide and 1.35 g (3 millimoles of D-α-aminobenzylpenicillin triethylamine salt are dissolved in a mixture of 25 ml of chloroform and 15 ml of dimethylformamide. The solution is stirred at 0° to 5° C for 15 hours. After the reaction is completed, the solution is treated in the same manner as described in Example 1-(3). 1.81 g of 6-[D-2-(D-2-(o-nitrophenylsulfenylamino)-3-N-methylcarbamoyl-propionamido)-2phenylacetamido]penicillanic acid are obtained as yellow needles. M.p. 145° -147° C(decomp.)

Infrared absorption spectrum:
$\nu_{max.}^{nujol}$: 3250, 1780, 1725, 1630 cm$^{-1}$ 2. 1.80 g (2.86 millimoles) of 6-[D-2-(D-2-(o-nitrophenylsulfenylamino)-3-N-methylcarbamoyl-propionamido)-2-phenylacetamido]penicillanic acid and 1.23 g (8.98 millimoles of thiobenzamide are dissolved in a mixture of 30 ml of methanol and 5 ml of tetrahydrofuran. The solution is stirred at room temperature for 20 minutes. The reaction solution is treated in the same manner as described in Example 1-(4). 1.23 g of 6-[D-2-(D-2-amino-3N-methylcarbamoyl-propionamido)-2-phenylacetamido]penicillanic acid are obtained as colorless powder. M.p. 193° - 195° C(decomp.)

Infrared absorption spectrum:
$\nu_{max.}^{nujol}$: 3275, 1760, 1650 cm$^{-1}$

Thin layer chromatography:
Rf = 0.45 (Silica gel plate, Solvent: n-butanol-acetic acid-water (4 : 1 : 1))

Infrared absorption spectrum of the potassium salt:
$\nu_{max.}^{nujol}$: 3290, 1765, 1650, 1600 cm$^{-1}$

EXAMPLE 10

1. 1.60 g (4 millimoles) of N-[L-2-(o-nitrophenylsulfenylamino)-3-N-methylcarbamoyl-propionyloxy]succinimide and 1.80 g (4 millimoles) of D-α-aminobenzylpenicillin triethylamine salt are dissolved in 25 ml of dimethylformamide. The solution is stirred at 0° to 5° C for 16 hours. After the reaction, the solution is treated in the same manner as described in Example 1-(3). 2.45 g of 6-[D-2-(L-2-(o-nitrophenylsulfenylamino)-3-N-methylcarbamoyl-propionamido)-2-phenylacetamido]penicillanic acid are obtained as yellow needles. M.p. 144° - 146° C(decomp.)

Infrared absorption spectrum:
$\nu_{max.}^{nujol}$: 3250, 1770, 1730, 1635 cm$^{-1}$ 2. 2.40 g (3.81 millimoles) of 6-[D-2-(L-2-(o-nitrophenylsulfenylamino)-3-N-methylcarbamoyl-propionamido)-2-phenylacetamido]penicillanic acid and 1.80 g (13.14 millimoles) of thiobenzamide are dissolved in a mixture of 30 ml of methanol and 25 ml of tetrahydrofuran. The solution is stirred at room temperature for 30 minutes. Then, the reaction solution is treated in the same manner as described in Example 1-(4). 1.51 g of 6-[D-2-(L-2-amino-3-N-methylcarbamoyl-propionamido)-2-phenyacetamido]penicillanic acid are obtained as colorless powder. M.p. 191 - 193° C(decomp.)

Infrared absorption spectrum:
$\nu_{max.}^{nujol}$: 3270, 1760, 1650 cm$^{-1}$

Thin layer chromatography:
Rf = 0.45 (Silica gel plate, Solvent: n-butanol-acetic acid- water (4 : 1 : 1))

Infrared absorption spectrum of the potassium salt:
$\nu_{max.}^{nujol}$: 3300, 1765, 1650, 1600 cm$^{-1}$

EXAMPLE 11

1. 1.6 g (10 millimoles) of DL-2-amino-3-N-ethylcarbamoyl-propionic acid (i.e., DL-N'-ethyl-asparagine), 2 g of o-nitro-phenylsulfenyl chloride 20 ml of water, 8 ml of tetrahydrofuran and 1.9 g of potassium carbonate are treated in the same manner as described in Example 1-(1). 1.7 g of DL-2-(o-nitrophenylsulfenylamino)-3-N-ethylcarbamoyl-propionic acid are obtained. M.p. 178° - 180° C (decomp.)

2. 850 mg (2.7 millimoles) of DL-2-(o-nitrophenylsulfenylamino)-3-N-ethylcarbamoyl-propionic acid, 577 mg of dicyclohexylcarbodiimide, 322 mg of N-hydroxysuccinimide and 20 ml of tetrahydrofuran are treated in the same manner as described in Example 1-(2). 850 mg of N-[DL-2-(o-nitrophenylsulfenylamino)-3-N-ethylcarbamoyl-propionyloxy]succinimide are obtained as yellow caramel.

3. 820 mg (2 millimoles) of N-[DL-2-(o-nitrophenylsulfenylamino)-3-N-ethylcarbamoyl-propionyloxy]succinimide and 900 mg (2 millimoles) of D-α-aminobenzylpenicillin triethylamine salt are dissolved in 15 ml of dimethylformamide. The solution is stirred at 0° to 5° C for 16 hours. After the reaction, the solution is treated in the same manner as described in Example 1-(3). 1.19 g of 6-[D-2-(DL-2-(o-nitrophenylsulfenylamino)-3-N-ethylcarbamoyl-propionamido)-2-phenylacetamido]-penicillanic acid are obtained as caramel.

Infrared absorption spectrum:
$\nu_{max}.^{nujol}$: 3270, 1770, 1720, 1640 cm$^{-1}$ 4. 1.15 g (1.78 millimoles) of 6-[D-2-(DL-2-(o-nitrophenylsulfenylamino)-3-N-ethylcarbamoyl-propionamido)-2-phenylacetamido]penicillanic acid and 822 mg (6 millimoles) of thiobenzamide are dissolved in a mixture of 20 ml of methanol and 2 ml of tetrahydrofuran. The solution is stirred at room temperature for 20 minutes. The reaction solution is then treated in the same manner as described in Example 1-(4). 600 mg of 6-[D-2-(DL-2-amino-3-N-ethylcarbamoyl-propionamido)-2-phenylacetamido]penicillanic acid are obtained. M.p. 190° - 193° C (decomp.)

Infrared absorption spectrum:
$\nu_{max}.^{nujol}$: 3270, 1760, 1650 cm$^{-1}$

Thin layer chromatography:
Rf = 0.475 (Silica gel plate, Solvent: n-butanol-acetic acid-water (4 : 1 : 1))

Infrared absorption spectrum of the potassium salt:
$\nu_{max}.^{nujol}$: 3280, 1765, 1650, 1600 cm$^{-1}$

EXAMPLE 12

1. 1.75 g (10 millimoles) of DL-2-amino-3-N-n-propylcarbamoyl-propionic acid (i.e., DL-N'-n-propyl-asparagine), 2.2 g of o-nitrophenylsulfenyl chloride, 20 ml of water, 10 ml of tetrahydrofuran and 2.2 g of potassium carbonate are treated in the same manner as described in Example 1-(1). 2.2 g of DL-2-(o-nitrophenylsulfenylamino)-3-N-n-propylcarbamoyl-propionic acid are obtained. M.p. 200° - 205° C (decomp.)

2. 1.9 g (6 millimoles) of DL-2-(o-nitrophenylsulfenylamino)-3-N-propylcarbamoyl-propionic acid, 1.3 g of dicyclohexylcarbodiimide, 700 mg of N-hydroxysuccinimide and 20 ml of tetrahydrofuran are treated in the same manner as described in Example 1-(2). 2.4 g of N-[DL-2-(o-nitrophenylsulfenylamino)-3-N-n-propylcarbamoyl-propionyloxy]succinimide are obtained as yellow caramel.

3. 450 mg (1.06 millimoles) of N-[DL-2-(o-nitrophenylsulfenylamino)-3-N-n-propylcarbamoyl-propionyloxy]succinimide and 495 mg (1.1 millimoles) of D-α-aminobenzylpenicillin triethylamine salt are dissolved in 15 ml of dimethylformamide. The solution is stirred at 0° to 5° C for 16 hours. After the reaction, the solution is treated in the same manner as described in Example 1-(3). 230 mg of 6-[D-2(DL-2-(o-nitrophenylsulfenylamino)-3-N-n-propylcarbamoyl-propionamido)-2-phenylacetamido]penicillanic acid are obtained as caramel.

Infrared absorption spectrum:
$\nu_{max}.^{nujol}$: 3280, 1770, 1725, 1645 cm$^{-1}$ 4. 210 mg (0.31 millimole) of 6-[D-2-(DL-2-(o-nitrophenylsulfenylamino)-3-N-n-propylcarbamoyl-propionamido)-2-phenylacetamido]penicillanic acid and 137 mg (1.0 millimole) of thiobenzamide are dissolved in 10 ml of methanol. The solution is stirred at room temperature for 20 minutes. The reaction solution is treated in the same manner as described in Example 1-(2). 75 mg of 6-[D-2-(DL-2-amino-3-N-n-propylcarbamoyl-propionamido)-2-phenylacetamido]penicillanic acid are obtained. M.p. 175° - 178° C (decomp.)

Infrared absorption spectrum:
$\nu_{max}.^{nujol}$: 3250, 1765, 1650 cm$^{-1}$

Thin layer chromatography:
Rf = 0.55 (Silica gel plate, Solvent: n-butanol-acetic acid-water (4 : 1 : 1))

EXAMPLE 13

1. A solution of 13.5 g of DL-N-(o-nitrophenylsulfenyl) aspartic anhydride in 20 ml of tetrahydrofuran and 30 ml of methanol is heated at 50° to 60° C for 30 minutes. The solvent is removed under reduced pressure. The residue is dissolved in 100 ml of tetrahydrofuran, and 5.1 g of N-hydroxysuccinimide and 9.1 g of dicyclohexylcarbodiimide are added thereto. Then, the mixture is allowed to stand at room temperature for 17 hours. Urea precipitate is removed by filtration, and the filtrate is evaporated under reduced pressure to remove solvent. 14.2 g of N-[DL-3-(o-nitrophenylsulfenylamino)-3-methoxycarbonyl-propionyloxy]succinimide are obtained. M.p. 158° - 160° C (decomp.)

2. A solution of 2.4 g of N-[DL-3-(o-nitrophenylsulfenylamino)-3-methoxycarbonyl-propionyloxy]succinimide and 1.5 g of n-butylamine in 25 ml of tetrahydrofuran is allowed to stand at room temperature for 2 days. The solution is evaporated under reduced pressure to remove solvent. 1.8 g of methyl DL-2-(o-nitrophenylsulfenylamino)-3-N-n-butylcarbamoyl-propionate are obtained. M.p. 104° - 105° C.

3. To a solution of 1.7 g of methyl DL-2-(o-nitrophenylsulfenylamino)-3-N-n-butylcarbamoyl-propionate in 30 ml of methanol, 2 ml of hydrazine hydrate are dissolved. After one hour, yellow crystals are collected by filtration. 1.2 g of DL-2-(o-nitrophenylsulfenylamino)-3-N-n-butylcarbamoyl-propionyl hydrazide are obtained. M.p. 180° - 182° C.

4. To a solution of 888 mg of DL-2-(o-nitrophenylsulfenylamino)-3-N-n-butylcarbamoyl-propionyl hydrazide in 15 ml of tetrahydrofuran containing 5 ml of 10% sulfuric acid and 5 ml of acetic acid, 345 mg of sodium nitrite are added portionwise at −5° to −10° C. After 20 minutes, 20 ml of cold water are added to the reaction mixture. The mixture is then extracted with 20 ml of ethyl acetate. The extract is dried and then evaporated under reduced pressure to remove solvent. 700 mg of DL-2-(o-nitrophenylsulfenylamino)-3-N-n-butylcarbamoyl-propionyl azide are obtained as yellow caramel.

5. 700 mg (1.9 millimoles) of DL-2-(o-nitrophenylsulfenylamino)-3-N-n-butylcarbamoyl-propionylazide and 900 mg (2 millimoles) of D-α-aminobenzylpenicillin triethylamine salt are dissolved in 15 ml of chloroform. The solution is stirred at 0° to 5° C for 48 hours. After the reaction, the solution is treated in the same manner as described in Example 1-(1). 210 mg of 6-[D-2-(DL-2-(o-nitrophenylsulfenylamino)-3-N-n-butylcarbamoyl-propionamido)-2-phenylacetamido]penicillanic acid are obtained as yellow caramel.

Infrared absorption spectrum:
$\nu_{max}.^{nujol}$: 3300, 1780, 1725, 1640 cm$^{-1}$ 6. 200 mg (0.3 millimoles) of 6-[D-2-(DL-2-(o-nitrophenylsulfenylamino)-3-N-n-butylcarbamoyl-propionamido)-2-phenylacetamido]penicillanic acid and 300 mg (2.19 millimoles) of thiobenzamide are dissolved in a mixture of 10 ml of methanol and one ml of tetrahydrofuran. The solution is stirred at room temperature for 30 minutes. Then, the reaction solution is treated in the same manner as described in Example 1-(4). 85 mg of 6-[D-2-(DL-2-amino-3-N-n-butylcarbamoyl-propionamido)-2-phenylacetamido]penicillanic acid are obtained as a colorless powder. M.p. 190° – 193° C (decomp.)
Infrared absorption spectrum:
$v_{max.}^{nujol}$: 3375, 1665, 1645 cm$^{-1}$
Thin layer chromatography:
Rf = 0.51 (Silica gel plate, Solvent: n-butanol-acetic acid-water (4 : 1 : 1))

EXAMPLE 14

1. 1.76 g (10 millimoles) of DL-2-amino-3-N-β-hydroxyethylcarbamoyl-propionic acid (i.e., DL-N'-β-hydroxyethyl-asparagine), 2.2 g of o-nitrophenylsulfenyl chloride, 20 ml of water, 10 ml of tetrahydrofuran and 2.2 g of potassium carbonate are treated in the same manner as described in Example 1-(1). 2.1 g of DL-2-(o-nitrophenylsulfenylamino)-3-N-β-hydroxyethylcarbamoyl-propionic acid are obtained. M.p. 123° –125° C.

2. 1.64 g (5 millimoles) of DL-2-(o-nitrophenylsulfenylamino)-3-N-β-hydroxyethylcarbamoyl-propionic acid, 1.13 g of dicyclohexylcarbodiimide, 633 mg of N-hydroxysuccinimide and 40 ml of tetrahydrofuran are treated in the same manner as described in Example 1-(2). 1.7 g of N-[DL-2-(o-nitrophenylsulfenylamino)-3-N-β-hydroxyethylcarbamoyl-propionyloxy]succinimide are obtained as yellow caramel.

3. 852 mg (2.0 millimoles) of N-[DL-2-(o-nitrophenylsulfenylamino)-3-N-β-hydroxyethylcarbamoyl-propionyloxy]succinimide and 675 mg (1.5 millimoles) of D-α-aminobenzylpenicillin triethylamine salt are dissolved in 30 ml of chloroform. The solution is stirred at 0° to 5° C for 16 hours. After the reaction, the solution is treated in the same manner as described in Example 1-(3). 550 mg of 6-[D-2-(DE-2-(o-nitrophenylsulfenylamino)-3-N-β-hydroxyethylcarbamoyl-propionamido)-2-phenylacetamido]penicillanic acid are obtained as yellow caramel.
Infrared absorption spectrum:
$v_{max.}^{nujol}$: 3270, 1770, 1720, 1650 cm$^{-1}$ 4. 500 mg (0.76 millimole) of 6-[D-2-(DL-2-(o-nitrophenylsulfenylamino)-3-N-β-hydroxyethylcarbamoyl-propionamido)-2-phenylacetamido]penicillanic acid and 390 mg (2.8 millimoles) of thiobenzamide are dissolved in a mixture of 10 ml of methanol and 2 ml of tetrahydrofuran. The solution is stirred at room temperature for 20 minutes. Then, the reaction solution is treated in the same manner as described in Example 1-(4). 280 mg of 6-[D-2-(DL-2-amino-3-N-β-hydroxyethylcarbamoyl-propionamido)-2-phenylacetamido]penicillanic acid are obtained as colorless powder. M.p. 177° – 180° C (decomp.)
Infrared absorption spectrum:
$v_{max.}^{nujol}$: 3260, 1760, 1655 cm$^{-1}$
Thin layer chromatography:
Rf = 0.49 (Silica gel plate, Solvent: n-butanol-acetic acid-water (4 : 1 : 1))

EXAMPLE 15

1. 1.61 g (10 millimoles) of DL-2-amino-3-N-dimethylcarbamoyl-propionic acid (i.e., DL-N'-dimethyl-asparagine), 2.1 g of o-nitrophenylsulfenyl chloride, 20 ml of water, 15 ml of tetrahydrofuran and 2.1 g of potassium carbonate are treated in the same manner as described in Example 1-(1). 1.9 g of DL-2-(o-nitrophenylsulfenylamino)-3-N-dimethylcarbamoyl-propionic acid are obtained. M.p. 144° – 146° C.

2. 1.39 g (4.3 millimoles of DL-2-(o-nitrophenylsulfenylamino)-3-N-dimethylcarbamoyl-propionic acid, 936 mg of dicyclohexylcarbodiimide, 518 mg of N-hydroxysuccinimide and 40 ml of tetrahydrofuran are treated in the same manner as described in Example 1-(2). 1.6 g of N-[DL-2-(o-nitrophenylsulfenylamino )-3-N-dimethylcarbamoyl-propionyloxy]succinimide are obtained. M.p. 126° – 128° C (decomp.)

3. 820 mg (2 millimoles) of N-[DL-2-(o-nitrophenylsulfenylamino)-3-N-dimethylcarbamoyl-propionyloxy]-succinimide and 900 mg (2 millimoles) of D-α-aminobenzylpenicillin triethylamine salt are dissolved in a mixture of 15 ml of chloroform and 13 ml of dimethylformamide. The solution is stirred at 0° to 5° C for 16 hours. After the reaction, the solution is treated in the same manner as described in Example 1-(1). 1.22 g of 6-[D-2-(DL-2-(o-nitrophenylsulfenylamino)-3-N-dimethylcarbamoyl-propionamido)-2-phenylacetamido]penicillanic acid are obtained as yellow caramel.
Infrared absorption spectrum:
$v_{max.}^{nujol}$: 3200, 1780, 1730, 1630 cm$^{-1}$ 4. 1.21 g (1.88 millimoles) of 6-[D-2-(DL-2-(o-nitrophenylsulfenylamino)-3-N-dimethylcarbamoyl-propionamido)-2-phenylacetamido]penicillanic acid and 1.03 g (7.50 millimoles) of thiobenzamide and dissolved in a mixture of 30 ml of methanol and 10 ml of tetrahydrofuran. The solution is stirred at room temperature for 20 minutes. Then, the reaction solution is treated in the same manner as described in Example 1-(4). 660 mg of 6-[D-2-(DL-2-amino-3-N-dimethylcarbamoyl-propionamido)-2-phenylacetamido]penicillanic acid are obtained. M.p. 192° – 194° C (decomp.)
Infrared absorption spectrum:
$v_{max.}^{nujol}$: 3240, 1770, 1630 cm$^{-1}$
Thin layer chromatography:
Rf = 0.451 (Silica gel plate, Solvent: n-butanol-acetic acid-water (4 : 1 : 1))
Infrared absorption spectrum of the potassium salt:
$v_{max.}^{nujol}$: 3240, 1760, 1590 cm$^{-1}$

EXAMPLE 16

1. 720 mg (2 millimoles) of DL-2-benzyloxycarbonylamino-3-benzyloxycarbonyl-propionic acid and 210 mg (2 millimoles) of triethylamine are dissolved in 7 ml of dichloromethane, and a solution of 270 mg (2 millimoles) of isobutyl chlorocarbonate in 2 ml of dichloromethane is added thereto at −20° to −15° C. Ten minutes after said addition, a solution of 740 mg (2 millimoles) of D-α-aminobenzylpenicillin triethylamine salt in 4 ml of dimethylformamide is added dropwise to the solution. The mixture is stirred at −15° to −10° C for 30 minutes and then at −10° to 0° C for 30 minutes. After the reaction, the mixture is evaporated at about 30° C under reduced pressure to remove solvent. 5 ml of an aqueous 5% citric acid solution and 10 ml of ethyl acetate are added to the residue obtained, and the organic solvent layer is separated therefrom. The organic solvent layer is washed with water, dried and then mixed with 200 ml of triethylamine (2 millimoles). The mixture thus obtained is evaporated at about 30° C under reduced pressure to remove solvent. 970 mg of 6-[D-2-(DL-2-benzyloxycarbonylamino-3-benzyloxycarbonyl-propionamido)-2-phenylacetamido]penicillanic acid triethylamine salt are obtained as colorless crystals. M.p. 110° – 113° C (decomp.)
Infrared absorption spectrum:
$v_{max.}^{nujol}$: 3300, 1775, 1735, 1690, 1660, 1610, 1520 cm$^{-1}$ 2. 200 mg (0.3 millimole) of 6-[D-2-(DL-2-benzyloxycarbonylamino-3-benzyloxycarbonyl-propionamido)-2-phenylacetamido]penicillanic acid triethylamine salt are dissolved in 6 ml of ethanol, and 300 mg of 30% palladium-BaCO₃ are added to the solution. The solution is shaken at room temperature in hydrogen gas for 4 hours under atmospheric pressure. After the reaction, insoluble materials are removed by filtration, and the filtrate is evaporated at about 30° C under reduced pressure to remove solvent. 5 ml of ether are added to the residue obtained. Then, the white precipitates thus obtained are collected by filtration, washed with chloroform and dried. 60 mg of 6-[D-2-(DL-2-amino-3-hydroxycarbonyl-propionamido)-2-phenylacetamido]-penicillanic acid triethylamine salt re obtained. M.p. 189° - 191° C (decomp.)

Infrared absorption spectrum:
$v_{max.}^{nujol}$: 3300, 1750, 1665, 1595, 1540 cm⁻¹
Thin layer chromatography:
Rf = 0.36 (Silica gel plate, Solvent: n-butanolacetic acid-water (4 : 1 : 1))

EXAMPLE 17

1. 9.2 g (50 millimoles) of DL-2-amino-3-methoxycarbonyl-propionic acid hydrochloride (i.e., DL-aspartic acid O^β-methyl ester HCl), 10.5 g of o-nitrophenylsulfenyl chloride, 50 ml of water, 70 ml of tetrahydrofuran and 24.3 g of potassium carbonate are treated in the same manner as described in Example 1-(1). 9.8 g of DL-2-(o-nitrophenylsulfenylamino)-3-methoxycarbonyl-propionic acid are obtained. M.p. 108°- 109° C.

2. 9 g (30 millimoles) of DL-2-(o-nitrophenylsulfenylamino)-3-methoxycarbonyl-propionic acid, 6.7 g of dicyclohexylcarbodiimide, 4 g of N-hydroxysuccinimide and 80 ml of tetrahydrofuran are treated in the same manner as described in Example 1-(2). 11 g of N-[DL-2-(o-nitrophenylsulfenylamino)-3-methoxycarbonyl-propionyloxy]succinimide are obtained. M.p. 125° - 127° C.

3. 794 mg (2 millimoles) of N-[DL-2-(o-nitrophenylsulfenylamino)-3-methoxycarbonyl-propionyloxy]succinimide and 900 mg (2 millimoles) of D-α-aminobenzylpenicillin triethylamine salt are dissolved in a mixture of 25 ml of chloroform and 4 ml of dimethylformamide. The solution if stirred at 0° to 5° C for 15 hours. After the reaction, the solution is treated in the same manner as described in Example 1-(3). 1.2 g of 6-[D-2-(DL-2-(o-nitrophenylsulfenylamino)-3-methoxycarbnyl-propionamido)-2 -phenylacetamido]penicillanic acid are obtained as yellow caramel.

Infrared absorption spectrum:
$v_{max.}^{liq.}$: 3300, 1780, 1725, 1650 cm⁻¹

4. 1.20 g (1.90 millimoles) of 6-[D-2(DL-2-(o-nitrophenylsulfenylamino)-3methoxycarbonyl-propionamido)-2-phenylacetamido]penicillanic acid and 800 mg (5.84 millimoles) of thiobenzamide are dissolved in a mixture of 20 ml of methanol and 3 ml of tetrahydrofuran. The solution is stirred at room temperature for 45 minutes. Then, the reaction solution is treated in the same manner as described in Example 1-(4). 1.51 g of 6-[D-2-(DL-2-amino-3-methoxycarbonyl-propionamido)-2-phenylacetamido]penicillanic acid are obtained as colorless powder. M.p. 185° - 188° C (decomp.)

Infrared absorption spectrum:
vmax.^nujol: 3250, 1760, 1730, 1660 cm⁻¹
Thin layer chromatography:
Rf = 0.453 (Silica gel plate, Solvent: n-butanol-acetic acid-water (4 : 1 : 1))
Infrared absorption spectrum of the potassium salt:
$v_{max.}^{nujol}$: 3280, 1760, 1730, 1650, 1595 cm⁻¹

The following compound is prepared in the same manner as described above.

6-[D-2-(D-2-amino-3-methoxycarbonyl-propionamido)-2-p-hydroxyphenylacetamido]penicillanic acid: M.p. 170° - 173° C (decomp.)

Infrared absorption spectrum:
$v_{max.}^{nujol}$: 3300, 1760, 1720, 1650, 1600 cm⁻¹
Thin layer chromatography:
Rf = 0.42 (Silica gel plate, Solvent: n-butanol-acetic acid-water (4 : 1 : 1))

EXAMPLE 18

1. 18.4 g (100 millimoles) of D-2-amino-3-methoxycarbonyl-propionic acid hydrochloride (i.e., D-aspartic acid O^β-methyl ester HCl), 20 g of o-nitrophenylsulfenyl chloride, 80 ml of water, 80 ml of tetrahydrofuran and 26 g of potassium carbonate are treated in the same manner as described in Example 1-(1). 18 g of D-2-(o-nitrophenylsulfenylamino)-3-methoxycarbonyl-propionic acid are obtained. M.p. 86° - 87° C.

2. 3 g (10 millimoles) of D-2-(o-nitrophenylsulfenylamino)-3-methoxycarbonyl-propionic acid, 2.3 g of dicyclohexylcarbodiimide, 1.35 g of N-hydroxysuccinimide and 30 ml of tetrahydrofuran are treated in the same manner as described in Example 1-(2). 3.5 g of N-[D-2-(o-nitrophenylsulfenylamino)-3-methoxycarbonyl-propionyloxy]succinimide are obtained. M.p. 133° C (decomp.)

3. 794 mg (2 millimoles) of N-[D-2-(o-nitrophenylsulfenylamino)-3-methoxycarbonyl-propionyloxy]succinimide and 900 mg (2 millimoles) of D-α-aminobenzylpenicillin triethylamine salt are dissolved in 25 ml of chloroform. The solution is stirred at 0° to 5° C for 16 hours. After the reaction, the solution is treated in the same manner as described in Example 1-(3). 1.15 g of 6-[D-2-(D-2-(o-nitrophenylsulfenylamino)-3-methoxycarbonylpropionamido)-2-phenylacetamido]penicillanic acid are obtained as caramel.

Infrared absorption spectrum:
$v_{max.}^{nujol}$: 3270, 1775, 1720, 1640 cm⁻¹

4. 1.10 g (1.74 millimoles) of 6-[D-2-(D-2-(o-nitrophenylsulfenylamino)-3-methoxycarbonyl-propionamido)-2-phenylacetamido]penicillanic acid and 835 mg (6.1 millimoles) of thiobenzamide are dissolved in a mixture of 30 ml of methanol and 5 ml of tetrahydrofuran. The solution is stirred at room temperature for 40 minutes. Then, the reaction solution is treated in the same manner as described in Example 1-(4). 680 mg of 6-[D-2-(D-2-amino-3methoxycarbonyl-propionamido)-2-phenylacetamido] penicillanic acid are obtained. M.p. 185 - 188° C (decomp.)

Infrared absorption spectrum:
$v_{max.}^{nujol}$: 3250, 1765, 1725 (ester), 1655 cm⁻¹
Thin layer chromatography:
Rf = 0.453 (Silica gel plate, Solvent: n-butanol-acetic acid-water (4 : 1 : 1))

EXAMPLE 19

1. 720 mg (2 millimoles) of benzyl DL-2-benzyloxycarbonylamino-3-carboxy-propionate and 210 mg (2.1 millimoles) of triethylamine are dissolved in 7 ml of dichloromethane, and a solution of 270 mg (2 millimoles) of isobutyl chloroformate in 2 ml of dichloromethane is added thereto at −20° to −15° C. Ten minutes after said addition, a solution of 990 mg (2.2 millimoles) of D-α-aminobenzylpenicillin triethylamine salt in 5 ml of chloroform is added dropwise to the solution. Then, the mixture is treated in the same manner as described in Example 16-(1). 1.30 g of 6-[D-2-(DL-3-benzyloxycarbonylamino-3-benzyloxycarbonyl-propionamido)-2-phenylacetamido]penicillanic acid triethylamine salt are obtained as colorless powder. M.p. 115° - 119° C (decomp.)

Infrared absorption spectrum:
$v_{max.}^{nujol}$: 3300, 1775, 1730, 1660, 1610, 1500 cm$^{-1}$ 2. 660 mg (0.83 millimole) of 6-[D-2-(DL-3-benzyloxycarbonylamino-3-benzyloxycarbonyl-propionamido)-2-phenylacetamido]penicillanic acid triethylamine salt are dissolved in 20 ml of ethanol, and 500 mg of 30% palladium-BaCO$_3$ are added to the solution. The solution is shaken at room temperature in hydrogen gas for 2 hours under atmospheric pressure. Then, the reaction solution is treated in the same manner as described in Example 16 -(2). 220 mg of 6-[D-2(DL-3-amino-hydroxycarbonyl-propionamido)-2-phenylacetamido]-penicillanic acid triethylamine salt are obtained as pale grey powder. M.p. 185° - 188° C (decomp.)

Infrared absorption spectrum:
$v_{max.}^{nujol}$: 3250, 1770, 1650, 1600, 1530 cm$^{-1}$ Thin layer chromatography:
Rf = 0.28 (Silica gel plate, Solvent: n-butanol-acetic acid-water (4 : 1 : 1))

EXAMPLE 20

(1) 1.6 g (10 millimoles) of DL-3-amino-3-N-ethylcarbamoyl-propionic acid (i.e., DL-N'-ethyl-isoasparagine), 2.2 g of o-nitrophenylsulfenyl chloride, 20 g of water, 20 ml of tetrahydrofuran and 2.3 g of potassium carbonate are treated in the same manner as described in Example 1-(1). 2.0 g of DL-3-(o-nitrophenylsulfenylamino)-3-N-ethylcarbamoyl-propionic acid are obtained. M.p. 165° - 167° C (decomp.)

2. 1.05 g (3.35 millimoles) of DL-3-(o-nitrophenylsulfenylamino)-3-N-ethylcarbamoyl-propionic acid, 700 mg of dicyclohexylcarbodiimide, 391 mg of N-hydroxysuccinimide and 40 ml of tetrahydrofuran are treated in the same manner as described in Example 1-(2). 1.2 g of N-[DL-3-(o-nitrophenylsulfenylamino)-3-N-ethylcarbamoyl-propionyloxy]succinimide are obtained. M.p. 157 - 158° C.

3. 820 mg (2 millimoles) of N-[Dl-3-(o-nitrophenylsulfenylamino)-3-N-ethylcarbamoyl-propionyloxy]succinimide and 900 mg (2 millimoles) of D-α-aminobenzylpenicillin triethylamine salt are dissolved in 15 ml of dimethylformamide. The solution is stirred at 0° to 5° C for 16 hours. After the reaction, the solution is treated in the same manner as described in Example 1-(3). 1.09 g of 6-[D-2-(DL-3-(o-nitrophenylsulfenylamino)-3-N-ethylcarbamoyl-propionamido)-2-phenylacetamido]-penicillanic acid are obtained as caramel.

Infrared absorption spectrum:
$\mu_{max.}^{nujol}$: 3260, 1775, 1725, 1620 cm$^{-1}$ 4. 1.05 g (1.63 millimoles) of 6-[D-2-(DL-3-(o-nitrophenylsulfenylamino)-3-N-ethylcarbamoyl-propionamido)-2-phenylacetamido]penicillanic acid and 781 mg (5.7 millimoles) of thiobenzamide are dissolved in a mixture of 30 ml of methanol and 5 mil of tetrahydrofuran. The solution is stirred at room temperature for 45 minutes. Then, the reaction solution is treated in the same manner as described in Example 1-(4). 730 mg of 6-[D-2-(DL-3-N-ethylcarbamoyl-propionamido)-2-phenylacetamido]penicillanic acid are obtained. M.p. 200° - 203° C (decomp.)

Infrared absorption spectrum:
$v_{max.}^{nujol}$: 3290, 1765, 1655 cm$^{-1}$

Thin layer chromatography:
Rf = 0.475 (Silica gel plate, Solvent: n-butanol-acetic acid-water (4 : 1 : 1))

EXAMPLE 21

1. 1.75 g (10 millimoles) of DL-3-amino-3-N-n-propylcarbamoyl-propionic acid (i.e., DL-N'-n-propyl-isoasparagine), 2.2 g of o-nitrophenylsulfenyl chloride, 20 ml of water, 20 ml of tetrahydrofuran and 2.3 g of potassium carbonate are treated in the same manner as described in Example 1-(1). 2.8 g of DL-3-(o-nitrophenylsulfenylamino)-3-N-n-propylcarbamoyl-propionic acid are obtained. M.p. 148° - 150° C (decomp.)

2. 981 mg (3 millimoles) of DL-3-(o-nitrophenylsulfenylamino)-3-N-n-propylcarbamoyl-propionic acid, 618 mg of dicyclohexylcarbodiimide, 345 mg of N-hydroxysuccinimide and 40 ml of tetrahydrofuran are treated in the same manner as described in Example 1-(2). 1.1 g of N-[DL-3-(o-nitrophenylsulfenylamino)-3-N-n-propylcarbamoyl-propionyloxy]succinimide are obtained as yellow caramel.

3. 848 mg (2 millimoles) of N-[DL-3-(o-nitrophenylsulfenylamino)-3-N-propylcarbamoyl-propionyloxy]succinimide and 900 mg (2 millimoles) of D-α-aminobenzylpenicillin triethylamine salt are dissolved in 20 ml of dimethylformamide. The solution is stirred at 0° to 5° C for 16 hours. After the reaction, the solution is treated in the same manner as described in Example 1-(3). 800 mg of 6-[D-2-(DL-3-(o-nitrophenylsulfenylamino)-3-N-m-propylcarbamoyl-propionamido-2-phenylacetamide]penicillanic acid are obtained as caramel.

Infrared absorption spectrum:
$v_{max.}^{nujol}$: 3275, 1775, 1725, 1635 cm$^{-1}$ 4 780 mg (1.17 millimoles) of 6-[D-2-(DL-3-(o-nitrophenylsulfenylamino)-3-N-n-propylcarbamoyl-propionamido)-2-phenylacetamido]penicillanic acid and 561 mg (4.1 millimoles) of thiobenzamide are dissolved in a mixture of 15 ml of methanol and 2 ml of tetrahydrofuran. The solution is stirred at room temperature for 20 minutes. Then, the reaction solution is treated in the same manner as described in Example 1-(4). 390 mg of 6-[D-2-(DL-3-amino- 3-N-n-propylcarbamoyl-propionamido)-2-phenylacetamido]-penicillanic acid are obtained. M.p. 181 - 184° C (decomp.)

Infrared absorption spectrum:
$v_{max.}^{nujol}$: 3280, 1770, 1660 cm$^{-1}$

Thin layer chromatography:
Rf = 0.55 (Silica gel plate, Solvent: n-butanolacetic acid-water (4 : 1 : 1))

EXAMPLE 22

1. 1.6 g (10 millimoles) of DL-3-amino-3-N-dimethylcarbamoyl-propionic acid (i.e., DL-N'-dimethyl-isoasparagine), 2.2 g of o-nitrophenylsulfenyl chloride, 20 ml of water, 20 ml of tetrahydrofuran and 2.2 g of potassium carbonate are treated in the same manner as described in Example 1-(1). 1.9 g of DL-3-(o-nitrophenylsulfenylamino)-3-N-dimethylcarbamoyl-propionic acid are obtained. M.p. 144° - 146° C.

2. 1.88 g (6 millimoles) of DL-3-(o-nitrophenylsulfenylamino)-3-N-dimethylcarbamoyl-propionic acid, 1.24 g of dicyclohexylcarbodiimide, 748 mg of N-hydroxysuccinimide and 40 ml of tetrahydrofuran are treated in the same manner as described in Example 1-(2). 900 mg of N-[DL-3-(o-nitrophenylsulfenylamino)-3-N-dimethylcarbamoyl-propionyloxy]succinimide are obtained. M.p. 171° - 172° C.

3. 820 mg (2 millimoles) of N-[DL-3-(o-nitrophenyl-sulfenylamino)-3-N-dimethylcarbamoyl-propionyloxy]-succinimide and 900 mg (2 millimoles) of D-α-aminobenzylpenicillin triethylamine salt are dissolved in a mixture of 25 ml of chloroform and 12 ml of dimethylformamide. The solution is stirred at 0° to 5° C for 18 hours. After the reaction, the solution is treated in the same manner as described in Example 1-(3). 1.25 g of 6-[D-2-(DL-3-(o-nitrophenylsulfenylamino)-3-N-dimethylcarbamoyl-propionamido)-2-phenylacetamido]-penicillanic acid are obtained as yellow caramel.

Infrared absorption spectrum:
$v_{max.}^{nujol}$: 3270, 1780, 1725, 1630 cm$^{-1}$ 4. 1.20 g (1.86 millimoles) of 6-[D-2-(DL-3-(o-nitrophenylsulfenylamino)-3-N-dimethylcarbamoyl-propionamido)-2-phenylacetamido]penicillanic acid and 800 mg (5.80 millimoles) of thiobenzamide are dissolved in a mixture of 20 ml of methanol and 3 ml of tetrahydrofuran. The solution is stirred at room temperature for 30 minutes. Then, the reaction solution is treated in the same manner as described in Example 1-(4). 810 mg of 6-[D-2-(DL-3-amino-3-N-dimethylcarbamoyl-propionamido)-2-phenylacetamido]penicillanic acid are obtained as a colorless powder. M.p. 207° – 210° C (decomp.)

Infrared absorption spectrum:
$v_{max.}^{nujol}$: 3250, 1760, 1645 cm$^{-1}$

Thin layer chromatography:
Rf = 0.392 (Silica gel plate, Solvent: n-butanolacetic acid-water (4 : 1 : 1))

Infrared absorption spectrum of the potassium salt:
$v_{max.}^{nujol}$: 3260, 1760, 1640, 1595 cm$^{-1}$

EXAMPLE 23

1. 3.82 g of N-[D-2-(o-nitrophenylsulfenylamino)-3-carbamoyl-propionyloxy]succinimide are dissolved in 60 ml of tetrahydrofuran. 12.5 ml of an aqueous 1 N-sodium hydroxide solution containing 2.3 g of p-hydroxy-D-phenylglycine are added to the solution. The mixture is stirred at room temperature for 24 hours. 20 ml of ethyl acetate and 20 ml of water are added to the reaction mixture, and said mixture is shaken. Then, the aqueous layer is separated therefrom, adjusted to pH 3 with citric acid and extracted with a mixture of 20 ml of tetrahydrofuran and 10 ml of ethyl acetate. The extract is washed with water, dried and evaporated to remove solvent. The residue thus obtained is washed with ether. 3.47 g of D-2-(D-2-(o-nitrophenylsulfenylamino)-3-carbamoyl-propionamido)-2-p-hydroxyphenylacetic acid are obtained as yellow needles. M.p. 133° – 135° C. (decomp).

Infrared absorption spectrum:
$v_{max.}^{nujol}$: 3380 (broad), 3270, 1705, 1670, 1635 cm$^{-1}$ Thin layer chromatography:
Rf = 0.39 (Silica gel plate, Solvent: ethyl acetate-methanol-acetic acid (10 : 1 : 1))

2. 435 mg of D-2-(D-2-(o-nitrophenylsulfenylamino)-3-carbamoyl-propionamido)-2-p-hydroxyphenylacetic acid and 121 mg of dimethylaniline are dissolved in a mixture of 2 ml of dimethylformamide and 3 ml of anhydrous tetrahydrofuran. A solution of 136 mg of isobutyl chlorocarbonate in 2 ml of tetrahydrofuran is added to the mixture at −25° to −20° C under stirring. Five minutes later, a solution of 382 mg of 6-aminopenicillanic acid triethylamine salt in 2.5 ml of water is added to the mixture at −10° to −8° C, and the mixture is stirred at −10° to −5° C for 40 minutes and then at −5° to 0° C for 30 minutes. After the reaction, the mixture is adjusted to pH 3 with an aqueous 5% citric acid solution and extracted with a mixture of 10 ml of tetrahydrofuran and 5 ml of ethyl acetate. The extract is washed with water, dried and then evaporated at below 40° C to remove solvent. Ether is added to the residue obtained, and crystalline precipitates are collected by filtration. 530 mg of 6-[D-2-(D-2-(o-nitrophenylsulfenylamino)-3-carbamoyl-propionamido)-2-p-hydroxyphenylacetamido]penicillanic acid are obtained as yellow needles. M.p. 130° – 132° C (decomp.)

Infrared absorption spectrum:
$v_{max.}^{nujol}$: 3280, 1775, 1730, 1650 cm$^{-1}$ Thin layer chromatography:
Rf = 0.30 (Silica gel plate, Solvent: ethyl acetatetetrahydrofuran-acetic acid (10:10:1))

3. 800 mg of 6-[D-2-(D-2-(o-nitrophenylsulfenylamino)-3-carbamoyl-propionamido)-2-p-hydroxyphenylacetmido]cillanic acid and 410 mg of thiobenzamide are dissolved in a mixture of 2 ml of tetrahydrofuran and 8 ml of ethanol. The solution is stirred at room temperature for 15 minutes. The reaction solution is evaporated at below 30° C to remove solvent. Tetrahydrofuran is added to the residue, and pale yellow crystalline precipitates are collected by filtration. The precipitates are dissolved in 30 ml of water, insoluble materials are removed by filtration, and the filtrate is freeze-dried. The colorless powder thus obtained is suspended in 3 ml of methanol. 100 mg of triethylamine and 180 mg of potassium 2-ethylhexanoate are added to the suspension. Then, ether is added to the suspension, and crystalline precipitates are collected by filtration. 370 mg of potassium 6-[D-2-(D-2-amino-3-carbamoyl-propionamido)-2-p-hydroxyphenylacetamido]penicillanate are obtained as a colorless crystalline powder. M.p. 213° – 215° C (decomp.) Free base: M.p. 202° – 205° C (decomp.)

EXAMPLE 24

1. 3 g (23.6 millimoles) of D-2-amino-3-N-methylcarbamoyl-propionic acid hydrochloride (i.e., D-N'-methylasparagine HCl), 4.5 g of benzyloxycarbonyl chloride, 30 g of water, 30 ml of tetrahydrofuran and 12 g of potassium carbonate are treated in the same manner as described in Example 1-(1). 5.1 g of D-2-benzyloxycarbonylamino-3-N-methylcarbamoyl-propionic acid are obtained. M.p. 142° – 143° C.

2. 2.8 g (10 millimoles) of D-2-benzyloxycarbonylamino-3-N-methylcarbamoyl-propionic acid, 2.27 g of dicyclohexylcarbodiimide, 1.27 g of N-hydroxysuccinimide and 120 ml of tetrahydrofuran are treated in the same manner as described in Example 1-(2). 2.6 g of N-(D-2-benzyloxycarbonylamino-3-N-methylcarbamoyl-propionyloxy)succinimide are obtained. M.p. 132° – 134° C.

3. 3.75 g of N-(D-2-benzyloxycarbonylamino-3-N-methylcarbamoyl-propionyloxy)succinimide are dissolved in 50 ml of tetrahydrofuran. 12.5 ml of an aqueous 1 N-sodium hydroxide solution containing 2.3 g of p-hydroxy-D-phenylglycine are added to the solution. The mixture is stirred at room temperature for 24 hours. Then, the reaction mixture is treated in the same manner as described in Example 23-(1). 3.0 g of D-2-(D-2-benzyloxycarbonylamino-3-N-methylcarbamoyl-propionamido)-2-p-hydroxyphenylacetic acid are obtained as colorless crystalline powder. M.p. 154° – 156° C (decomp.)

Infrared absorption spectrum:
$v_{max.}^{nujol}$: 3300, 1790, 1650, 1640 cm$^{-1}$ Thin layer chromatography:

scribed in Example 16-(1). 1.30 g of 6-[D-2-(DL-3-benzyloxycarbonylamino-3-benzyloxycarbonyl-propionamido)-2-phenylacetamido]penicillanic acid triethylamine salt are obtained as colorless powder. M.p. 115° – 119° C (decomp.)

Infrared absorption spectrum:
$\nu_{max}.^{nujol}$: 3300, 1775, 1730, 1660, 1610, 1500 cm$^{-1}$ 2. 660 mg (0.83 millimole) of 6-[D-2-(DL-3-benzyloxycarbonylamino-3-benzyloxycarbonyl-propionamido)-2-phenylacetamido]penicillanic acid triethylamine salt are dissolved in 20 ml of ethanol, and 500 mg of 30% palladium-BaCO$_3$ are added to the solution. The solution is shaken at room temperature in hydrogen gas for 2 hours under atmospheric pressure. Then, the reaction solution is treated in the same manner as described in Example 16 -(2). 220 mg of 6-[D-2(DL-3-amino--hydroxycarbonyl-propionamido)-2-phenylacetamido]-penicillanic acid triethylamine salt are obtained as pale grey powder. M.p. 185° – 188° C (decomp.)

Infrared absorption spectrum:
$\nu_{max}.^{nujol}$: 3250, 1770, 1650, 1600, 1530 cm$^{-1}$ Thin layer chromatography:
Rf = 0.28 (Silica gel plate, Solvent: n-butanol-acetic acid-water (4 : 1 : 1))

EXAMPLE 20

(1) 1.6 g (10 millimoles) of DL-3-amino-3-N-ethylcarbamoyl-propionic acid (i.e., DL-N'-ethyl-isoasparagine), 2.2 g of o-nitrophenylsulfenyl chloride, 20 g of water, 20 ml of tetrahydrofuran and 2.3 g of potassium carbonate are treated in the same manner as described in Example 1-(1). 2.0 g of DL-3-(o-nitrophenylsulfenylamino)-3-N-ethylcarbamoyl-propionic acid are obtained. M.p. 165° – 167° C (decomp.)

2. 1.05 g (3.35 millimoles) of DL-3-(o-nitrophenylsulfenylamino)-3-N-ethylcarbamoyl-propionic acid, 700 mg of dicyclohexylcarbodiimide, 391 mg of N-hydroxysuccinimide and 40 ml of tetrahydrofuran are treated in the same manner as described in Example 1-(2). 1.2 g of N-[DL-3-(o-nitrophenylsulfenylamino)-3-N-ethylcarbamoyl-propionyloxy]succinimide are obtained. M.p. 157 – 158° C.

3. 820 mg (2 millimoles) of N-[Dl-3-(o-nitrophenylsulfenylamino)-3-N-ethylcarbamoyl-propionyloxy]succinimide and 900 mg (2 millimoles) of D-α-aminobenzylpenicillin triethylamine salt are dissolved in 15 ml of dimethylformamide. The solution is stirred at 0° to 5° C for 16 hours. After the reaction, the solution is treated in the same manner as described in Example 1-(3). 1.09 g of 6-[D-2-(DL-3-(o-nitrophenylsulfenylamino)-3-N-ethylcarbamoyl-propionamido)-2-phenylacetamido]-penicillanic acid are obtained as caramel.

Infrared absorption spectrum:
$\mu_{max}.^{nujol}$: 3260, 1775, 1725, 1620 cm$^{-1}$ 4. 1.05 g (1.63 millimoles) of 6-[D-2-(DL-3-(o-nitrophenylsulfenylamino)-3-N-ethylcarbamoyl-propionamido)-2-phenylacetamido]penicillanic acid and 781 mg (5.7 millimoles) of thiobenzamide are dissolved in a mixture of 30 ml of methanol and 5 mil of tetrahydrofuran. The solution is stirred at room temperature for 45 minutes. Then, the reaction solution is treated in the same manner as described in Example 1-(4). 730 mg of 6-[D-2-(DL-3-N-ethylcarbamoyl-propionamido)-2-phenylacetamido]penicillanic acid are obtained. M.p. 200° – 203° C (decomp.)

Infrared absorption spectrum:
$\nu_{max}.^{nujol}$: 3290, 1765, 1655 cm$^{-1}$

Thin layer chromatography:

Rf = 0.475 (Silica gel plate, Solvent: n-butanol-acetic acid-water (4 : 1 : 1))

EXAMPLE 21

1. 1.75 g (10 millimoles) of DL-3-amino-3-N-n-propylcarbamoyl-propionic acid (i.e., DL-N'-n-propyl-isoasparagine), 2.2 g of o-nitrophenylsulfenyl chloride, 20 ml of water, 20 ml of tetrahydrofuran and 2.3 g of potassium carbonate are treated in the same manner as described in Example 1-(1). 2.8 g of DL-3-(o-nitrophenylsulfenylamino)-3-N-n-propylcarbamoyl-propionic acid are obtained. M.p. 148° – 150° C (decomp.)

2. 981 mg (3 millimoles) of DL-3-(o-nitrophenylsulfenylamino)-3-N-n-propylcarbamoyl-propionic acid, 618 mg of dicyclohexylcarbodiimide, 345 mg of N-hydroxysuccinimide and 40 ml of tetrahydrofuran are treated in the same manner as described in Example 1-(2). 1.1 g of N-[DL-3-(o-nitrophenylsulfenylamino)-3-N-n-propylcarbamoyl-propionyloxy]succinimide are obtained as yellow caramel.

3. 848 mg (2 millimoles) of N-[DL-3-(o-nitrophenylsulfenylamino)-3-N-propylcarbamoyl-propionyloxy]succinimide and 900 mg (2 millimoles) of D-α-aminobenzylpenicillin triethylamine salt are dissolved in 20 ml of dimethylformamide. The solution is stirred at 0° to 5° C for 16 hours. After the reaction, the solution is treated in the same manner as described in Example 1-(3). 800 mg of 6-[D-2-(DL-3-(o-nitrophenylsulfenylamino)-3-N-m-propylcarbamoyl-propionamido-2-phenylacetamide]penicillanic acid are obtained as caramel.

Infrared absorption spectrum:
$\nu_{max}.^{nujol}$: 3275, 1775, 1725, 1635 cm$^{-1}$ 4 780 mg (1.17 millimoles) of 6-[D-2-(DL-3-(o-nitrophenylsulfenylamino)-3-N-n-propylcarbamoyl-propionamido)-2-phenylacetamido]penicillanic acid and 561 mg (4.1 millimoles) of thiobenzamide are dissolved in a mixture of 15 ml of methanol and 2 ml of tetrahydrofuran. The solution is stirred at room temperature for 20 minutes. Then, the reaction solution is treated in the same manner as described in Example 1-(4). 390 mg of 6-[D-2-(DL-3-amino- 3-N-n-propylcarbamoyl-propionamido)-2-phenylacetamido]-penicillanic acid are obtained. M.p. 181 – 184° C (decomp.)

Infrared absorption spectrum:
$\nu_{max}.^{nujol}$: 3280, 1770, 1660 cm$^{-1}$

Thin layer chromatography:
Rf = 0.55 (Silica gel plate, Solvent: n-butanolacetic acid-water (4 : 1 : 1))

EXAMPLE 22

1. 1.6 g (10 millimoles) of DL-3-amino-3-N-dimethylcarbamoyl-propionic acid (i.e., DL-N'-dimethyl-isoasparagine), 2.2 g of o-nitrophenylsulfenyl chloride, 20 ml of water, 20 ml of tetrahydrofuran and 2.2 g of potassium carbonate are treated in the same manner as described in Example 1-(1). 1.9 g of DL-3-(o-nitrophenylsulfenylamino)-3-N-dimethylcarbamoyl-propionic acid are obtained. M.p. 144° – 146° C.

2. 1.88 g (6 millimoles) of DL-3-(o-nitrophenylsulfenylamino)-3-N-dimethylcarbamoyl-propionic acid, 1.24 g of dicyclohexylcarbodiimide, 748 mg of N-hydroxysuccinimide and 40 ml of tetrahydrofuran are treated in the same manner as described in Example 1-(2). 900 mg of N-[DL-3-(o-nitrophenylsulfenylamino)-3-N-dimethylcarbamoyl-propionyloxy]succinimide are obtained. M.p. 171° – 172° C.

3. 820 mg (2 millimoles) of N-[DL-3-(o-nitrophenylsulfenylamino)-3-N-dimethylcarbamoyl-propionyloxy]succinimide and 900 mg (2 millimoles) of D-α-aminobenzylpenicillin triethylamine salt are dissolved in a mixture of 25 ml of chloroform and 12 ml of dimethylformamide. The solution is stirred at 0° to 5° C for 18 hours. After the reaction, the solution is treated in the same manner as described in Example 1-(3). 1.25 g of 6-[D-2-(DL-3-(o-nitrophenylsulfenylamino)-3-N-dimethylcarbamoyl-propionamido)-2-phenylacetamido]penicillanic acid are obtained as yellow caramel.

Infrared absorption spectrum:
$v_{max.}^{nujol}$: 3270, 1780, 1725, 1630 cm$^{-1}$ 4. 1.20 g (1.86 millimoles) of 6-[D-2-(DL-3-(o-nitrophenylsulfenylamino)-3-N-dimethylcarbamoyl-propionamido)-2-phenylacetamido]penicillanic acid and 800 mg (5.80 millimoles) of thiobenzamide are dissolved in a mixture of 20 ml of methanol and 3 ml of tetrahydrofuran. The solution is stirred at room temperature for 30 minutes. Then, the reaction solution is treated in the same manner as described in Example 1-(4). 810 mg of 6-[D-2-(DL-3-amino-3-N-dimethylcarbamoyl-propionamido)-2-phenylacetamido]penicillanic acid are obtained as a colorless powder. M.p. 207° – 210° C (decomp.)

Infrared absorption spectrum:
$v_{max.}^{nujol}$: 3250, 1760, 1645 cm$^{-1}$

Thin layer chromatography:
Rf = 0.392 (Silica gel plate, Solvent: n-butanolacetic acid-water (4 : 1 : 1))

Infrared absorption spectrum of the potassium salt:
$v_{max.}^{nujol}$: 3260, 1760, 1640, 1595 cm$^{-1}$

EXAMPLE 23

1. 3.82 g of N-[D-2-(o-nitrophenylsulfenylamino)-3-carbamoyl-propionyloxy]succinimide are dissolved in 60 ml of tetrahydrofuran. 12.5 ml of an aqueous 1 N-sodium hydroxide solution containing 2.3 g of p-hydroxy-D-phenylglycine are added to the solution. The mixture is stirred at room temperature for 24 hours. 20 ml of ethyl acetate and 20 ml of water are added to the reaction mixture, and said mixture is shaken. Then, the aqueous layer is separated therefrom, adjusted to pH 3 with citric acid and extracted with a mixture of 20 ml of tetrahydrofuran and 10 ml of ethyl acetate. The extract is washed with water, dried and evaporated to remove solvent. The residue thus obtained is washed with ether. 3.47 g of D-2-(D-2-(o-nitrophenylsulfenylamino)-3-carbamoyl-propionamido)-2-p-hydroxyphenylacetic acid are obtained as yellow needles. M.p. 133° – 135° C. (decomp).

Infrared absorption spectrum:
$v_{max.}^{nujol}$: 3380 (broad), 3270, 1705, 1670, 1635 cm$^{-1}$ Thin layer chromatography:
Rf = 0.39 (Silica gel plate, Solvent: ethyl acetate-methanol-acetic acid (10 : 1 : 1))

2. 435 mg of D-2-(D-2-(o-nitrophenylsulfenylamino)-3-carbamoyl-propionamido)-2-p-hydroxyphenylacetic acid and 121 mg of dimethylaniline are dissolved in a mixture of 2 ml of dimethylformamide and 3 ml of anhydrous tetrahydrofuran. A solution of 136 mg of isobutyl chlorocarbonate in 2 ml of tetrahydrofuran is added to the mixture at −25° to −20° C under stirring. Five minutes later, a solution of 382 mg of 6-aminopenicillanic acid triethylamine salt in 2.5 ml of water is added to the mixture at −10° to −8° C, and the mixture is stirred at −10° to −5° C for 40 minutes and then at −5° to 0° C for 30 minutes. After the reaction, the mixture is adjusted to pH 3 with an aqueous 5% citric acid solution and extracted with a mixture of 10 ml of tetrahydrofuran and 5 ml of ethyl acetate. The extract is washed with water, dried and then evaporated at below 40° C to remove solvent. Ether is added to the residue obtained, and crystalline precipitates are collected by filtration. 530 mg of 6-[D-2-(D-2-(o-nitrophenylsulfenylamino)-3-carbamoyl-propionamido)-2-p-hydroxyphenylacetamido]penicillanic acid are obtained as yellow needles. M.p. 130° – 132° C (decomp.)

Infrared absorption spectrum:
$v_{max.}^{nujol}$: 3280, 1775, 1730, 1650 cm$^{-1}$ Thin layer chromatography:
Rf = 0.30 (Silica gel plate, Solvent: ethyl acetatetetrahydrofuran-acetic acid (10:10:1))

3. 800 mg of 6-[D-2-(D-2-(o-nitrophenylsulfenylamino)-3-carbamoyl-propionamido)-2-p-hydroxyphenylacetmido]penicillanic acid and 410 mg of thiobenzamide are dissolved in a mixture of 2 ml of tetrahydrofuran and 8 ml of ethanol. The solution is stirred at room temperature for 15 minutes. The reaction solution is evaporated at below 30° C to remove solvent. Tetrahydrofuran is added to the residue, and pale yellow crystalline precipitates are collected by filtration. The precipitates are dissolved in 30 ml of water, insoluble materials are removed by filtration, and the filtrate is freeze-dried. The colorless powder thus obtained is suspended in 3 ml of methanol. 100 mg of triethylamine and 180 mg of potassium 2-ethylhexanoate are added to the suspension. Then, ether is added to the suspension, and crystalline precipitates are collected by filtration. 370 mg of potassium 6-[D-2-(D-2-amino-3-carbamoyl-propionamido)-2-p-hydroxyphenylacetamido]penicillanate are obtained as a colorless crystalline powder. M.p. 213° – 215° C (decomp.) Free base: M.p. 202° – 205° C (decomp.)

EXAMPLE 24

1. 3 g (23.6 millimoles) of D-2-amino-3-N-methylcarbamoyl-propionic acid hydrochloride (i.e., D-N'-methylasparagine HCl), 4.5 g of benzyloxycarbonyl chloride, 30 g of water, 30 ml of tetrahydrofuran and 12 g of potassium carbonate are treated in the same manner as described in Example 1-(1). 5.1 g of D-2-benzyloxycarbonylamino-3-N-methylcarbamoyl-propionic acid are obtained. M.p. 142° – 143° C.

2. 2.8 g (10 millimoles) of D-2-benzyloxycarbonylamino-3-N-methylcarbamoyl-propionic acid, 2.27 g of dicyclohexylcarbodiimide, 1.27 g of N-hydroxysuccinimide and 120 ml of tetrahydrofuran are treated in the same manner as described in Example 1-(2). 2.6 g of N-(D-2-benzyloxycarbonylamino-3-N-methylcarbamoyl-propionyloxy)succinimide are obtained. M.p. 132° – 134° C.

3. 3.75 g of N-(D-2-benzyloxycarbonylamino-3-N-methylcarbamoyl-propionyloxy)succinimide are dissolved in 50 ml of tetrahydrofuran. 12.5 ml of an aqueous 1 N-sodium hydroxide solution containing 2.3 g of p-hydroxy-D-phenylglycine are added to the solution. The mixture is stirred at room temperature for 24 hours. Then, the reaction mixture is treated in the same manner as described in Example 23-(1). 3.0 g of D-2-(D-2-benzyloxycarbonylamino-3-N-methylcarbamoyl-propionamido)-2-p-hydroxyphenylacetic acid are obtained as colorless crystalline powder. M.p. 154° – 156° C (decomp.)

Infrared absorption spectrum:
$v_{max.}^{nujol}$: 3300, 1790, 1650, 1640 cm$^{-1}$ Thin layer chromatography:

Rf = 0.37 (Silicate gel plate, Solvent: ethyl acetate-ethanol-acetic acid (10 : 1 : 1))

4. 429 mg of D-2-(D-2-benzyloxycarbonylamino-3-N-methylcarbamoyl-propionamido)-2-p-hydroxyphenylacetic acid and 382 mg of 6-aminopenicillanic acid triethylaine are dissolved in 10 ml of dimethylformamide. 303 mg of diphenylphosphoric azide [$N_3PO(OC_6H_5)_2$] and 110 mg of triethylamine are added to the solution at −5° C, and the mixture is stirred at −5° C for 15 hours. After the reaction, the mixture is adjusted to pH 3 with an aqueous 5% citric acid solution and extractd with a mixture of 15 ml of tetrahydrofuran and 10 ml of ethyl acetate. The extract is washed with water, dried and then evaporated at below 40° C to remove solvent. Ether is added to the residue obtained, and precipitates are collected by filtration. 509 mg of 6-[D-2-(D-2-benzyloxycarbonylamino-3-N-methylcarbamoyl-propionamido)-2-p-hydroxyphenylacetamido]penicillanic acid are obtained as a colorless powder.

Infrared absorption spectrum:
$v_{max.}^{nujol}$: 3280, 1770, 1720, 1640 cm$^{-1}$
Thin layer chromatography:
Rf = 0.663 (Silica gel plate, Solvent: tetrahydrofuran-methanol-acetic acid (50 : 3 : 3))

5. 627 mg of 6-[D-2-(D-2-benzyloxycarbonylamino-3-N-methylcarbamoyl-propionamido)-2-p-hydroxyphenylacetamido]penicillanic acid and 400 mg of 30% palladium-BaCO$_3$ are suspended in 10 ml of methanol. The suspension is shaken at room temperature for 30 minutes. Said shaking step is carried out in a hydrogen gas atmosphere under atmospheric pressure. After the reaction is completed, the catalysts are removed by filtration. The filtrate is evaporated at below 40° C to remove solvent, and ether is added to the residue. Then, a colorless crystalline powder is collected by filtration and washed with tetrahydrofuran. 443 mg of 6-[D-2-(D-2-amino-3-N-methylcarbamoyl-propionamido)-2-p-hydroxyphenylacetamido]penicillanic acid are obtained. M.p. 198° − 201° C (decomp.)

EXAMPLE 25

1. 3.96 g of N-[D-2-(o-nitrophenylsulfenylamino)-3-N-methylcarbamoyl-propionyloxy]succinimide are dissolved in 20 ml of dimethylformamide. 12.5 ml of an aqueous 1 N-sodium hydroxide solution containing 2.3 g of p-hydroxy-D-phenylglycine are added to the solution. The mixture is stirred at room temperature for 10 hours. 10 ml of ethyl acetate are added to the reaction mixture, and said mixture is shaken. Then, the aqueous layer is separated therefrom, adjusted to pH 3 with citric acid and treated in the same manner as described in Example 23-(1). 3.80 g of D-2-(D-2-(o-nitrophenylsulfenylamino)-3-N-methylcarbamoyl-propionamido)-2-p-hydroxyphenylacetic acid are obtained as yellow needles. M.p. 111° − 113° C (decomp.)

Infrared absorption spectrum:
$v_{max.}^{nujol}$: 3370, 3250, 1705, 1650, 1625 cm$^{-1}$
Thin layer chromatography:
Rf = 0.36 (Silica gel plate, Solvent: ethyl acetate-methanol-acetic acid (10:1:1))

2. 897 mg of D-2-(D-2-(o-nitrophenylsulfenylamino)-3-N-methylcarbamoyl-propionamido)-2-p-hydroxyphenylacetic acid, 655 mg of 6-aminopenicillanic acid succinimidomethyl ester and 230 mg of N-hydroxysuccinimide are dissolved in 10 ml of dimethylformamide. 412 mg of dicyclohexylcarbodiimide are added to the solution at −5° C under stirring, and the mixture is stirred at the same temperature for 5 hours. 10 ml of water are added to the reaction mixture, and the aqueous mixture is extracted with a mixture of 20 ml of tetrahydrofuran and 10 ml of ethyl acetate. The extract is washed with an aqueous 5% citric acid solution, an aqueous sodium bicarbonate solution and water, successively. Then, the extract is dried and evaporated at below 40° C to remove solvent. Ether is added to the residue, and the precipitates are collected by filtration. 1200 mg of 6-[D-2-(D-2-(o-nitrophenylsulfenylamino)-3-N-methylcarbamoyl-propionamido)-2-p-hydroxyphenylacetamido]penicillanic acid succinimidomethyl ester are obtained as yellow crystalline powder. M.p. 143° − 144° C (decomp.)

Infrared absorption spectrum:
$v_{max.}^{nujol}$: 3290, 1780, 1760, 1730, 1715, 1650 cm$^{-1}$
Thin layer chromatography:
Rf = 0.17 (Silica gel plate, Solvent: ethyl acetatetetrahydrofuran (2:1))

3. 755 mg of 6-[D-2-(D-2-(o-nitrophenylsulfenylamino)-3-N-methylcarbamoyl-propionamido)-2-p-hydroxyphenylacetamido]-penicillanic acid succinimidomethyl ester are dissolved in 5 ml of dimethylformamide. 250 mg of 2-ethylhexyl 2-mercaptoacetate sodium salt are added to the solution, and the mixture is allowed to stand at 0° C to 5° C for 40 minutes. 10 ml of water and 10 ml of ethyl acetate are added to the reaction mixture, and said mixture is shaken. Then, the aqueous layer is separated therefrom, adjusted to pH 3 with an aqueous 5% citric acid solution and extracted with a mixture of 20 ml of tetrahydrofuran and 10 ml of ethyl acetate. The extract is washed with water, dried and then evaporated at below 40° C to remove solvent. 590 mg of 6-[D-2-(D-2-(o-nitrophenylsulfenylamino)-3-N-methylcarbamoylpropionamido)-2-p-hydroxyphenylacetamido]penicillanic acid are obtained as yellow crystalline powder. M.p. 165° − 167° C (decomp.)

Infrared absorption spectrum:
$v_{max.}^{nujol}$: 3400, 3250, 1780, 1730, 1640 cm$^{-1}$
Thin layer chromatography:
Rf = 0.59 (Silica gel plate, Solvent: tetrahydrofuran-methanol-acetic acid (5:0.3:0.3))

4. 1.1 g of 6-[D-2-(D-2-(o-nitrophenylsulfenylamino)-3-N-methylcarbamoyl-propionamido)-2-p-hydroxyphenylacetamido]-penicillanic acid and 830 mg of thiobenzamide are treated in the same manner as described in Example 1-(4). 700 mg of 6-[D-2-(D-2-amino-3-N-methylcarbamoyl-propionamido)-2-p-hydroxyphenylacetamido]penicillanic acid are obtained as a colorless powder. M.p. 198° − 201° C (decomp.)

EXAMPLE 26

6-[D-2-(D-2-(o-nitrophenylsulfenylamino)-3-carbamoylpropionamido)-2-p-hydroxyphenylacetamido]-penicillanic acid is prepared in the same manner as described in Example 23-(2). 632 mg of this compound and 410 mg of thiobenzamide are dissolved in a mixture of 2 ml of tetrahydrofuran and 8 ml of methanol. The solution is stirred at room temperature for 30 minutes. The reaction solution is evaporated at below 40° C to remove solvent. 5 ml of tetrahydrofuran are added to the residue, and pale yellow crystalline precipitates are collected by filtration. After washing twice with tetrahydrofuran, the precipitates are dissolved in 10 ml of water, and insoluble materials are removed by filtration. The filtrate is washed twice with 4 ml of tetrahydrofuran-ethyl acetate (2:1) and freeze-dried. 410 mg of 6-[D-2-(D-2-amino-3-carbamoyl-propionamido)-2-p-hydroxyphenylacetamido]penicillanic acid are obtained as a pale yellow crystalline powder. M.p. 202° - 205° C (decomp.)

Infrared absorption spectrum:
$v_{max.}^{nujol}$: 3250, 1760, 1665, 1600 cm$^{-1}$
Thin layer chromatography:
Rf = 0.30 (Silica gel plate, Solvent: n-butanol-acetic acid-water (4:1:1))

EXAMPLE 27

1. 897 mg of D-2-(D-2-(o-nitrophenylsulfenylamino)-3-N-methylcarbamoyl-propionamido)-2-p-hydroxyphenylacetic acid and 202 mg of N-methylmorpholine are dissolved in 10 ml of dimethylformamide. A solution of 217 mg of ethyl chlorocarbonate in 2 ml of tetrahydrofuran is added to the solution at −25° to −20° C under stirring. One minute later, a solution of 764 mg of 6-aminopenicillanic acid triethylamine salt in 4 ml of water is added to the mixture at −10° to −8° C, and then the mixture is treated in the same manner as described in Example 23-(2). 1.33 g of 6-[D-2-(D-2-(o-nitrophenylsulfenylamino)-3-N-methylcarbamoyl-propionamido)-2-p-hydroxyphenylacetamido]penicillanic acid are obtained as yellow needles. M.p. 165° - 167° C (decomp.)

Infrared absorption spectrum:
$v_{max.}^{nujol}$: 3400, 3250, 1780, 1730, 1640 cm$^{-1}$
Thin layer chromatography:
Rf = 0.59 (Silica gel plate, Solvent: tetrahydrofuran-methanol-acetic acid (5:0.3:0.3))

2. 646 mg of 6-[D-2-(D-2-(o-nitrophenylsulfenylamino)-3-N-methylcarbamoyl-propionamido)-2-p-hydroxyphenylacetamido]-penicillanic acid and 274 mg of thiobenzamide are dissolved in a mixture of 8 ml of methanol and 2 ml of tetrahydrofuran. The solution is stirred at room temperature for 40 minutes. The reaction solution is then treated in the same manner as described in Example 26. 437 mg of 6-[D-2-(D-2-amino-3-N-methylcarbamoylpropionamido)-2-p-hydroxyphenylacetamido]penicillanic acid are obtained as a colorless crystalline powder. M.p. 198° - 201° C (decomp.)

EXAMPLE 28

870 mg of D-2-(D-2-(o-nitrophenylsulfenylamino)-3-carbamoyl-propionamido)-2-p-hydroxyphenylacetic acid and 202 mg of triethylamine are dissolved in 10 ml of dimethylformamide, and 550 mg of diphenylphosphoric azide are added thereto at −15° to −10° C. The solution is stirred at the same temperature for 5 minutes. 764 mg of 6-aminopenicillanic acid triethylamine salt are added to the solution, and the mixture is further stirred at −5° to 0° C for 15 hours. After the reaction, the mixture is treated in the same manner as described in Example 24-(4). The crude product thus obtained is washed with chloroform and ethyl acetate, successively. 925 mg of 6-[D-2-(D-2-(o-nitrophenylsulfenylamino-3-carbamoyl-propionamido)-2-p-hydroxyphenylacetamido]-penicillanic acid are obtained as a yellow crystalline powder. M.p. 130° - 132° C (decomp.) This product is treated in the same manner as described in Example 23-(3), whereby 6-[D-2-(D-2-amino-3-carbamoyl-propionamido)-2-p-hydroxyphenylacetamido]penicillanic acid is obtained.

EXAMPLE 29

1. 1.29 g of D-2-(D-2-benzyloxycarbonylamino-3-N-methylcarbamoyl-propionamido)-2-hydroxyphenylacetic acid and 1.01 g of 6-aminopenicillanic acid benzyl ester are dissolved in 20 ml of dimethylformamide. 575 mg of N-hydroxysuccinimide and 680 mg of dicyclohexylcarbodiimide are added to the solution at −15° C, and the mixture is stirred at 0° C for 20 hours. Then, the reaction mixture is treated in the same manner as described in Example 25-(2). 1.80 g of 6-[D-2-(D-2-benzyloxycarbonylamino-3-N-methylcarbamoyl-propionamido)-2-p-hydroxyphenylacetamido]-penicillanic acid benzyl ester are obtained as colorless needles. M.p. 107° - 110° C (decomp.)

2. 1.44 g of 6-[D-2-(D-2-benzyloxycarbonylamino-3-N-methylcarbamoyl-propionamido)-2-p-hydroxyphenylacetamido]penicillanic acid benzyl ester, 1.5 g of 30% palladium-BaCO$_3$ and 30 ml of 95% aqueous methanol are treated in the same manner as described in Example 24-(5). 620 mg of 6-[D-2-(D-2-amino-3-N-methylcarbamoyl-propionamido)-2-p-hydroxyphenylacetamido]penicillanic acid are obtained as a colorless crystalline powder. M.p. 198° - 201° C(decomp.)

EXAMPLE 30

1. 2.14 g of D-2-(D-2-benzyloxycarbonylamino-3-N-methylcarbamoyl-propionamido)-2-p-hydroxyphenylacetic acid and 610 mg of dimethylaniline are dissolved in 20 ml of dimethylformamide, and a solution of 690 mg of isobutyl chlorocarbonate in 10 ml of chloroform is added thereto at −40° C under stirring. 10 ml of a solution of D-2-(D-2-benzyloxycarbonylamino-3-N-methylcarbamoyl-propionamido)-2-p-hydroxyphenylacetic acid isobutyloxycarbonyl ester is obtained. On the other hand, 2.12 g of 6-(2-phenylacetamido)penicillanic acid benzyl ester (i.e., Penicillin G benzyl ester) and 5.0 ml of dimethylaniline are dissolved in 1,2-dichloroethane, and 1.15 g of phosphorus pentachloride is added thereto at −25° C. The penicillanic ester solution is stirred at −30° to −20° C for 1.5 hours, 20 ml of ethanol are added dropwise thereto at the same temperature and it is further stirred for 2 hours. 10 ml of the solution of D-2-(D-2-benzyloxycarbonylamino-3-N-methylcarbamoyl-propionamido)-2-p-hydroxyphenylacetic acid isobutyloxycarbonyl ester are added dropwise to the penicillanic ester solution at −30° to −20° C for 10 minutes, and then the mixture is stirred at the same temperature for 3.5 hours and at room temperature for 6 hours. After the reaction, the mixture is concentrated at below 30° C under reduced pressure. 20 ml of water and 25 ml of tetrahydrofuran are added to the residue, and the aqueous mixture is shaken. The organic solvent layer is separated from the aqueous mixture. The organic solvent layer is washed with 10 ml of an aqueous 5% citric acid solution, 10 ml of an aqueous sodium bicarbonate solution and 10 ml of an aqueous saturated sodium chloride solution, successively. Then, the organic solvent layer is dried and evaporated at below 40° C to remove solvent. Ether is added to the residue obtained, and crystalline precipitates are collected by filtration. 2.96 g of 6-[D-2-(D-2-benzyloxycarbonylamino-3-N-methylcarbamoylpropionamido)-2-p-hydroxyphenylacetamido]penicillanic acid benzyl ester are obtained as colorless needles. M.p. 107° - 110° C(decomp.)

Infrared absorption spectrum:
$v_{max.}^{nujol}$: 3270, 1780, 1735, 1690, 1635 cm$^{-1}$
Thin layer chromatography:
Rf = 0.38 (Silica gel plate, Solvent: ethyl acetate)

2. 1.44 g of 6-[D-2-(D-2-benzyloxycarbonylamino-3-N-methylcarbamoyl-propionamido)-2-p-hydroxyphenylacetamido]penicillanic acid benzyl ester are dissolved in 30 ml of 95% aqueous methanol. 1.5 g of 30% palladium-BaCO₃ are added to the solution, and the mixture is shaken at room temperature for one hour. Said shaking step is carried out in hydrogen gas atmosphere under atmospheric pressure. After the reaction, the catalysts are removed by filtration. The filtrate is evaporated at below 40° C to remove solvent. 5 ml of water are added to the residue obtained, and insoluble materials are removed by filtration. Then, the aqueous layer of the filtrate is freeze-dried. 620 mg of 6-[D-2-(D-2-amino-3-N-methylcarbamoyl-propionamido)-2-p-hydroxyphenylacetamido]penicillanic acid are obtained as colorless crystalline powder. M.p. 198° – 201° C(decomp.)

EXAMPLE 31

1. 2.24 g of D-2-(D-2-(o-nitrophenylsulfenylamino-3-N-methylcarbamoyl-propionamido)-2-p-hydroxyphenylacetic acid and 505 mg of N-methylmorpholine are dissolved in 10 ml of chloroform, and a solution of 543 mg of ethyl chlorocarbonate in 10 ml of chloroform is added thereto at −20° C under stirring. 20 ml of a chloroform solution of D-2-(D-2-(o-nitrophenylsulfenylamino)-3-N-methylcarbamoyl-propionamido)-2-p-hydroxyphenylacetic acid ethoxycarbonyl ester are obtained. On the other hand, 2.47 g of 6-(2-phenylacetamido)penicillanic acid phthalimidomethyl ester (i.e., Penicillin G phthalimidomethyl ester) and 4.5 ml of N-methylmorpholine are dissolved in 30 ml of chloroform, and 1.15 g phosphorus pentachloride are added thereto at −25° C. The penicillanic ester solution is stirred at −30° C to −20° C for 1.5 hours, 20 ml of ethanol are added thereto at the same temperature, and it is further stirred for 2 hours. 10 ml of the chloroform solution of D-2-(D-2-(o-nitrophenylsulfenylamino)-3-N-methylcarbamoyl-propionamido)-2-p-hydroxyphenylacetic acid ethoxycarbonyl ester are added dropwise to the penicillanic ester solution at −30° to −25° C for 10 minutes, and then the mixture is stirred at −30° to −25° C for 3.5 hours and then at room temperature for 5 hours. After the reaction, the mixture is treated in the same manner as described in Example 30-(1). 3.07 g of 6-[D-2-(D-2-(o-nitrophenylsulfenylamino)-3-N-methylcarbamoyl-propionamido)-2-p-hydroxyphenylacetamido]penicillanic acid phthalimidomethyl ester are obtained as yellow powder. M.p. 105° – 107° C(decomp.)

Infrared absorption spectrum:
$\nu_{max.}^{nujol}$: 3250, 1780, 1725, 1640 cm⁻¹
Thin layer chromatography:
Rf = 0.72 (Silica gel plate, Solvent: ethyl acetate-tetrahydrofuran-acetic acid (10 : 10 : 1))

2. 1.63 g of 6-[D-2-(D-2-(o-nitrophenylsulfenylamino)-3-N-methylcarbamoyl-propionamido)-2-p-hydroxyphenylacetamido]-penicillanic acid phthalimidomethyl ester are dissolved in 10 ml of dimethylformamide. 500 mg of n-octyl 2-mercaptoacetate sodium salt are added to the solution, and the mixture is stirred at 0° to 5° C for 40 minutes. 20 ml of water and 10 ml of ethyl acetate are added to the reaction mixture, and said mixture is shaken. Then, the aqueous layer is separated therefrom, acidified with an aqueous 5% citric acid solution and extracted with 30 ml of tetrahydrofuran-ethyl acetate (2 : 1). The extract is washed with 5 ml of an aqueous saturated sodium chloride solution, dried and then evaporated at below 40° C to remove solvent. Ether is added to the residue obtained, and crystalline precipitates are collected by filtration.

1.05 g of 6-[D-2-(D-2-(o-nitrophenylsulfenylamino)-3-N-methylcarbamoyl-propionamido)-2-p-hydroxyphenylacetamido]penicillanic acid are obtained as yellow needles. M.p. 165° – 167° C(decomp.)

3. 646 mg of 6-[D-2-(D-2-(o-nitrophenylsulfenylamino)-3-N-methylcarbamoyl-propionamido)-2-p-hydroxyphenylacetamido]-penicillanic acid and 280 mg of thiobenzamide are dissolved in 10 ml of methanol-tetrahydrofuran (4 : 1). The solution is stirred at room temperature for 40 minutes. The reaction solution is evaporated at below 40° C to remove solvent. 5 ml of tetrahydrofuran are added to the residue, and pale yellow precipitates are collected by filtration. The precipitates are washed with tetrahydrofuran. Then, 10 ml of water are added to the precipitates, and the insoluble materials are removed by filtration. The aqueous layer of the filtrate is washed twice with 4 ml of a mixture of tetrahydrofuran-ethyl acetate (2 : 1) and freeze-dried. 410 mg of 6-[D-2-(D-2-amino-3-N-methylcarbamoyl-propionamido)-2-p-hydroxphenylacetamido]penicillanic acid are obtained as a pale yellow crystalline powder. M.p. 198° – 201° C(decomp.)

EXAMPLE 32

1. 2.18 g of D-2-(D-2-(o-nitrophenylsulfenylamino-3-carbamoyl-propionamido)-2-p-hydroxyphenylacetic acid and 610 mg of dimethylaniline are dissolved in 10 ml of dichloromethane, and a solution of 690 mg of isobutyl chlorocarbonate in 10 ml of dichloromethane is added thereto at −30° C under stirring. 20 ml of a solution of D-2-(D-2-(o-nitrophenylsulfenylamino)-3-carbamoyl-propionamido)-2-p-hydroxyphenylacetic acid isobutyloxycarbonyl ester are obtained. On the other hand, 2.47 g of 6-(2-phenylacetamido)-penicillanic acid phthalimidomethyl ester(i.e., Penicillin G phthalimidomethyl ester) and 5.0 ml of dimethylaniline are dissolved in 30 ml of dichloromethane, and 1.15 g of phosphorus pentachloride are added thereto at −25° C. The penicillanic ester solution is stirred at −35° to −30° C for 3 hours, 20 ml of methanol are added thereto, and it is further stirred at the same temperature for 2 hours. 10 ml of the solution of D-2-(D-2-(o-nitrophenylsulfenylamino)-3-carbamoyl-propionamido)-2-p-hydroxyphenylacetic acid isobutyloxycarbonyl ester are added dropwise to the penicillanic ester solution at −30° to −20° C for 10 minutes. Then, the mixture is treated in the same manner as described in Example 30-(1). 2.9 g of 6-[D-2-(D-2-(o-nitrophenylsulfenylamino)-3-carbamoyl-propionamido)-2-p-hydroxyphenylacetamido]penicillanic acid phthalimidomethyl ester are obtained as yellow powder.

Infrared absorption spectrum:
$\nu_{max.}^{nujol}$: 3285, 1780, 1730, 1655 cm⁻¹

2. 801 mg of 6-[D-2-(D-2-(o-nitrophenylsulfenylamino)-3-carbamoyl-propionamido)-2-p-hydroxyphenylacetamido]penicillanic acid phthalimidomethyl ester, 250 mg of n-octyl 2-mercaptoacetate sodium salt and 5 ml of dimethylformamide are treated in the same manner as described in Example 31-(2). 595 mg of 6-[D-2-(D-2-(o-nitrophenylsulfenylamino)-3-carbamoyl-propionamido)-2-p-hydroxyphenylacetamido]penicillanic acid are obtained as yellow needles. M.p. 130° – 132° C(decomp.)

3. 632 mg of 6-[D-2-(D-2-(o-nitrophenylsulfenylamino)-3-carbamoyl-propionamido)-2-p-hydroxyphenylacetamido]penicillanic acid, 410 mg of thiobenzamide and 10 ml of methanol-tetrahydrofuran (4 : 1)

are treated in the same manner as described in Example 31-(3). 410 mg of 6-[D-2-(D-2-amino-3-carbamoyl-propionamido)-2-p-hydroxyphenylacetamido]penicillanic acid are obtained as a pale yellow powder. M.p. 202° - 205° C(decomp.)

EXAMPLE 33

1. 2.15 g of D-2-(D-2-benzyloxycarbonylamino-3-N-methylcarbamoyl-propionamido)-2-p-hydroxyphenylacetic acid and 610 mg of dimethylaniline are dissolved in 20 ml of 1,2-dichloroethane, and a solution of 690 mg of isobutyl chlorocarbonate in 10 ml of 1,2-dichloroethane is added thereto at −25° C under stirring. 30 ml of a solution of D-2-(D-2-benzyloxycarbonylamino-3-N-methylcarbamoyl-propionamido)-2-p-hydroxyphenylacetic acid isobutyloxycarbonyl ester is obtained. On the other hand, 2.47 g of 6-(2-phenylacetamido) penicillanic acid phthalimidomethyl ester (i.e., Penicillin G phthalimidomethyl ester) and 2.06 ml of dimethylaniline are dissolved in 30 ml of 1,2-dichloroethane, and 1.15 g of phosphorus pentachloride are added thereto at −25° C. The penicillanic ester solution is stirred at −30° to −20° C for 1.5 hours, 20 ml of ethanol are added dropwise thereto at the same temperature, and it is further stirred for 2 hours. 3.41 g of dimethylaniline are added to the penicillanic ester solution. Then, 30 ml of the solution of D-2-(D-benzyloxycarbonyl-amino-3-N-methylcarbamoyl-propionamido)-2-p-hydroxyphenylacetic acid isobutyloxycarbonyl ester are added dropwise to the penicillanic ester solution at −30° to −20° C for 10 minutes, and the mixture is stirred at the same temperature for 3.5 hours. After the reaction is completed, the mixture is concentrated at below 30° C under reduced pressure. 20 ml of water, 25 ml of tetrahydrofuran and 10 ml of ethyl acetate are added to the residue. The organic solvent layer is separated from the mixture, washed with water, dried and then evaporated at below 40° C to remove solvent. Ether is added to the residue obtained, and crystalline precipitates are collected by filtration. 3.3 g of 6-[D-2-(D-2-benzyloxycarbonylamino-3-N-methylcarbamoyl-propionamido)-2-p-hydroxyphenylacetamido]penicillanic acid phthalimidomethyl ester are obtained as colorless crystals. M.p. 120° - 122° C(decomp.)

Infrared absorption spectrum:
$\nu_{max}^{nujol}$: 3280, 1780, 1730, 1640 cm$^{-1}$
Thin layer chromatography:
Rf = 0.41 (Silica gel plate, Solvent: ethyl acetate-tetrahydrofuran (2 : 1)

2. 1.76 g of 6-[D-2-(D-2-benzyloxycarbonylamino-3-N-methylcarbamoyl-propionamido)-2-p-hydroxyphenylacetamido]penicillanic acid phthalimidomethyl ester are dissolved in 10 ml of dimethylformamide. 500 mg of n-octyl 2-mercaptoacetate sodium salt are added to the solution, and the mixture is stirred at 0° to 5° C for 40 minutes. Then, the reaction mixture is treated in the same manner as described in Example 31-(2). 1.02 g of 6-[D-2-(D-2-benzyloxycarbonylamino-3-N-methylcarbamoyl-propionamido)-2-p-hydroxyphenylacetamido]penicillanic acid are obtained as colorless caramel.

3. 6-[D-2-(D-2-benzyloxycarbonylamino-3-N-methylcarbamoylpropionamido)-2-p-hydroxyphenylacetamido]penicillanic acid is treated in the same manner as described in Example 30-(2), whereby 6-[D-2-amino-3-N-methylcarbamoyl-propionamido)-2-p-hydroxyphenylacetamido]penicillanic acid is obtained. M.p. 198° - 201° C(decomp.)

What we claim is:

1. A compound of the formula:

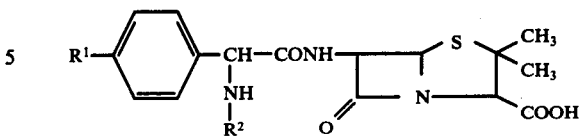

wherein $R^1$ is hydrogen or hydroxy, $R^2$ is a group of the formula: —CO-CH($NH_2$)—$CH_2COR^3$ or —COCH$_2$-CH($NH_2$)-COR$^3$, and R$^3$ is selected from the group consisting of hydroxy, lower alkylamino, di-lower alkylamino, lower alkoxy and hydroxy-lower alkylamino, or R$^3$ is amino when R$^1$ is hydroxy, or a pharmaceutically acceptable salt thereof.

2. The compound claimed in claim 1, in which R$^1$ is hydrogen or hydroxy, R$^2$ is a group of the formula: —CO-CH(NH$_2$)—CH$_2$COR$^3$ or —COCH$_2$—CH(NH$_2$)-COR$^3$, and R$^3$ is selected from the group consisting of hydroxy, lower alkylamino, di-lower alkylamino, lower alkoxy and hydroxy-lower alkylamino.

3. The compound claimed in claim 1, in which R$^1$ is hydrogen or hydroxy, R$^2$ is a group of the formula: —CO-CH(NH$_2$)—CH$_2$COR$^3$, and R$^3$ is lower alkylamino, di-lower alkylamino, lower alkoxy or hydroxy-lower alkylamino.

4. The compound claimed in claim 1, in which R$^1$ is hydroxy, R$^2$ is a group of the formula: —CO-CH(NH$_2$)-CH$_2$COR$^3$, and R$^3$ is lower alkylamino or lower alkoxy.

5. The compound claimed in claim 1, in which R$^1$ is hydrogen, R$^2$ is a group of the formula:—CO-CH(NH$_2$)-CH$_2$COR$^3$, and R$^3$ is lower alkylamino, di-lower alkylamino, lower alkoxy or hydroxy-lower alkylamino.

6. The compound claimed in claim 1, in which R$^1$ is hydrogen, R$^2$ is a group of the formula: —COCH$_2$-CH(NH$_2$)-COR$^3$, and R$^3$ is hydroxy, lower alkylamino or di-lower alkylamino.

7. The compound claimed in claim 1, in which R$^1$ is hydrogen or hydroxy, R$^2$ is a group of the formula: —CO-CH(NH$_2$)-CH$_2$COR$^3$, and R$^3$ is lower alkylamino.

8. The compound claimed in claim 1, in which R$^1$ is hydroxy, R$^2$ is a group of the formula: —CO-CH(NH$_2$)-CH$_2$COR$^3$, and R$^3$ is lower alkylamino.

9. The compound claimed in claim 4, in which R$^3$ is methylamino.

10. The compound claimed in claim 4, in which R$^3$ is isopropylamino.

11. The compound claimed in claim 4, in which R$^3$ is butylamino.

12. The compound claimed in claim 4, in which R$^3$ is n-hexylamino.

13. The compound in claim 4, in which R$^3$ is methoxy.

14. The compound claimed in claim 5, in which R$^3$ is methylamino.

15. The compound claimed in claim 5, in which R$^3$ is ethylamino.

16. The compound claimed in claim 5, in which R$^3$ dimethylamino.

17. The compound claimed in claim 5, in which R$^3$ is methoxy.

18. The compound claimed in claim 5, in which R$^3$ is β-hydroxymethylamino.

19. The compound claimed in claim 5, in which R$^3$ is n-butylamino.

20. The compound claimed in claim 6, in which R$^3$ is hydroxy.

21. The compound claimed in claim 6, in which $R^3$ is ethylamino.

22. The compound claimed in claim 6, in which $R^3$ is n-propylamino.

23. The compound claimed in claim 6, in which $R^3$ is dimethylamino.

24. 6-D-2-(D-2-amino-3-N-methylcarbamoyl-propionamido)-2-p-hydroxyphenylacetamido]penicillanic acid or a pharmaceutically acceptable salt thereof.

25. 6-[D-2-(D-2-amino-3-N-isopropylcarbamoyl-propionamido)-2-p-hydroxyphenylacetamido]penicillanic acid or a pharmaceutically acceptable salt thereof.

26. 6-[D-2-(D-2-amino-3-N-n-butylcarbamoyl-propionamido)-2-p-hydroxyphenylacetamido]penicillanic acid or a pharmaceutically acceptable salt thereof.

27. 6-[D-2-(D-2-amino-3-N-n-hexylcarbamoyl-propionamido)-2-p-hydroxyphenylacetamido]penicillanic acid or a pharmaceutically acceptable salt thereof.

28. 6-[D-2-(DL-2-amino-3-N-methylcarbamoyl-propionamido)-2-phenylacetamido]penicillanic acid or a pharmaceutically acceptable salt thereof.

29. 6-[D-2-(DL-2-amino-3-N-n-butylcarbamoyl-propionamido)-2-phenylacetamido]penicillanic acid or a pharmaceutically acceptable salt thereof.

30. 6-[D-2-(DL-3-amino-3-hydroxycarbonyl-propionamido)-2-phenylacetamido]penicillanic acid or a pharmaceutically acceptable salt thereof.

31. A pharmaceutical composition which is essentially consisting of an antimicrobially effective amount of the compound of claim 1 and a pharmaceutically acceptable carrier.

32. A pharmaceutical composition which is essentially consisting of an antimicrobially effective amount of the compound of claim 3 and a pharmaceutically acceptable carrier.

33. A pharmaceutical composition which is essentially consisting of an antimicrobially effective amount of the compound of claim 4 and a pharmaceutically acceptable carrier.

34. A pharmaceutical composition which is essentially consisting of an antimicrobially effective amount of the compound of claim 5 and a pharmaceutically acceptable carrier.

35. A pharmaceutical composition which is essentially consisting of an antimicrobially effective amount of the compound of claim 6 and a pharmaceutically acceptable carrier.

36. A pharmaceutical composition which is essentially consisting of an antimicrobially effective amount of the compound of claim 7 and a pharmaceutically acceptable carrier.

37. A pharmaceutical composition which is essentially consisting of an antimicrobially effective amount of the compound of claim 8 and a pharmaceutically acceptable carrier.

38. The composition of claim 31 wherein said effective amount is that which is necessary to produce an antimicrobial effect by administration to a warm-blooded animal.

39. The composition of claim 36 wherein said effective amount is that which is necessary to produce an antimicrobial effect by administration to a warm-blooded animal.

40. The composition of claim 37 wherein said effective amount is that which is necessary to produce an antimicrobial effect by administration to a warm-blooded animal.

41. The composition of claim 31 wherein said effective amount is 0.25 to 20 grams/adult human body/day.

42. The composition of claim 36 wherein said effective amount is 0.25 to 20 grams/adult human body/day.

43. The composition of claim 37 wherein said effective amount is 0.25 to 20 grams/adult human body/day.

* * * * *